United States Patent
Zhang et al.

(10) Patent No.: US 10,253,096 B2
(45) Date of Patent: Apr. 9, 2019

(54) ANTI-TIM-3 ANTIBODIES

(71) Applicant: Eli Lilly and Company, Indianapolis, IN (US)

(72) Inventors: Yi Zhang, Edison, NJ (US); Yang Shen, Scarsdale, NY (US); Carmine Carpenito, Hartsdale, NY (US); Yiwen Li, Woodcliff Lake, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 57 days.

(21) Appl. No.: 15/679,190

(22) Filed: Aug. 17, 2017

(65) Prior Publication Data

US 2018/0057591 A1 Mar. 1, 2018

Related U.S. Application Data

(60) Provisional application No. 62/469,753, filed on Mar. 10, 2017, provisional application No. 62/379,343, filed on Aug. 25, 2016.

(51) Int. Cl.
| | |
|---|---|
| *C07K 16/28* | (2006.01) |
| *A61K 45/06* | (2006.01) |
| *A61K 39/395* | (2006.01) |
| *A61N 5/10* | (2006.01) |
| *C12N 5/10* | (2006.01) |
| *A61K 39/00* | (2006.01) |

(52) U.S. Cl.
CPC ...... *C07K 16/2803* (2013.01); *A61K 39/3955* (2013.01); *A61K 45/06* (2013.01); *A61N 5/10* (2013.01); *A61K 2039/505* (2013.01); *A61K 2039/545* (2013.01); *C07K 2317/21* (2013.01); *C07K 2317/34* (2013.01); *C07K 2317/41* (2013.01); *C07K 2317/55* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,470,428 B2 | 12/2008 | Kuchroo et al. |
| 8,101,176 B2 | 1/2012 | Kuchroo et al. |
| 8,697,069 B2 | 4/2014 | Kuchroo et al. |
| 8,709,412 B2 | 4/2014 | Jones et al. |
| 2014/0044728 A1 | 2/2014 | Takayanagi et al. |
| 2015/0218274 A1 | 8/2015 | Sabatos-Peyton et al. |

FOREIGN PATENT DOCUMENTS

| | | |
|---|---|---|
| WO | 2015117002 A1 | 8/2015 |
| WO | 2016007513 A1 | 1/2016 |
| WO | 2016161270 A1 | 10/2016 |

OTHER PUBLICATIONS

Thies et al., J. Clin. Oncol. 20, (2002), pp. 2530-2536.
Fiori et al., Ann. Ist. Super Sanita 48 (2012), pp. 161-171.
Kang, C.W. et al., Sci. Rep. 5:15659 (2015).
Mahoney, et al., Cancer Immunotherapy, vol. 14, Aug. 2015, 561-584.
Haanen, et al., Seminars in Oncology, vol. 42, No. 3., Jun. 2015, pp. 423-428.
Sakuiski, et al., 10.1016/J.clim.2010.03.044, Clinical Immunology, 2010.
Huang, Yu-Hwa, et al., Nature, vol. 517, Jan. 15, 2015, 386-407.
Chiao-Wen Kang, Et Al: "Apoptosis of tumor infiltrating effector TIM-3+CD8+ T cells in colon cancer", Scientific Reports, vol. 5, No. 1, Oct. 23, 2015, p. 15659.
S.F. Ngiow, Et Al: "Anti-TIM3 Antibody Promotes T Cell IFN—Mediated Antitumor Immunity and Suppresses Established Tumors", Cancer Research, vol. 71, No. 10, Mar. 23, 2011, pp. 3540-3551.
Jean Da Silva Correia, Et Al "Identification and Characterization of a Potent Anti-Human TIM-3 Antagonist", AACR Conference: Tumor Immunology and Immunotherapy: A New Chapter, Dec. 2, 2014.

*Primary Examiner* — Hong Sang
(74) *Attorney, Agent, or Firm* — Robert Brian Johnson

(57) ABSTRACT

The present invention relates to antibodies that bind human T-cell immunoglobulin- and mucin-domain-containing protein-3 (Tim-3), and may be useful for treating solid and hematological tumors alone and in combination with chemotherapy and ionizing radiation.

30 Claims, No Drawings

Specification includes a Sequence Listing.

US 10,253,096 B2

ANTI-TIM-3 ANTIBODIES

The present invention is in the field of medicine. Particularly, the present invention relates to antibodies directed to T-cell immunoglobulin- and mucin-domain-containing protein-3 (Tim-3), compositions comprising such anti-Tim-3 antibodies, and methods of using such anti-Tim-3 antibodies for the treatment of solid and hematological tumors alone or in combination with chemotherapy and other cancer therapeutics.

Tumor cells escape detection and elimination by the immune system through a variety of mechanisms. One such mechanism is by the manipulation of immune checkpoint regulatory pathways that are normally used in the maintenance of self-tolerance and control of T cell activation. Cancer cells can commandeer these immune checkpoint regulatory pathways to suppress the anti-tumor response and prevent their destruction.

Although T cells recognizing tumor antigens can be isolated from patients and mouse models, such cells can exhibit an exhausted phenotype characterized by an impairment in cytotoxic functions, effector cytokine production, and proliferation. Moreover, such tumor-infiltrating T cells can express high levels of the checkpoint regulator Tim-3. In this regard, it has been shown that anti-Tim-3 antibodies can restore anti-tumor immunity in some murine cancer models.

Antibodies directed to human Tim-3 are known. Humanized antibodies against human Tim-3 are described in WO15117002. MBG453, an anti-human Tim-3 antibody, is also currently being tested in human clinical trials. However, no antibody targeting Tim-3 has been approved for therapeutic use in humans.

Tim-3 has been shown to interact with galectin-9 (SEQ ID NO:40), phosphadityserine ($C_{13}H_{24}NO_{10}P$), high-mobility group Box 1 (HMGB1), and carcinoembryonic antigen cell adhesion molecule 1 (CEACAM1) (SEQ ID NO:39). CEACAM1 expression in the primary tumors of melanoma patients has been shown to be associated with the subsequent development of metastatic disease (Thies et al., J. Clin. Oncol. 20, (2002), pp. 2530-2536). Additionally, CEACAM1 expression has been shown to be a prognosticator for unfavorable non-small cell lung cancer (NSCLC) related survival, an independent risk factor for lymph node metastasis of colon carcinomas, associated with urinary bladder cancer and muscle invasiveness, present on thyroid carcinoma cell lines derived from tumors showing aggressive behavior, and associated with a more malignant transformation in gastric carcinomas (Fiori et al., Ann. Ist. Super Sanita 48 (2012), pp. 161-171). With regards to galectin-9, tumor-derived galectin-9 has been shown to induce the apoptosis of tumor-infiltrating Tim-3$^+$ CD8$^+$ T cells in a CT26 mouse colon tumor model (Kang, C. W. et al., Sci. Rep. 5:15659 (2015).

Because all of the aforementioned Tim-3 ligands are not exclusive ligands of Tim-3, it is desirable to provide therapeutic anti-Tim-3 antibodies that differentially block the activity of said ligands as these ligands can regulate the immune system independently of Tim-3. Such a strategy can provide alternative ways to more specifically modulate Tim-3 activity, allowing for tailored immuno-oncology based therapies for patients. Furthermore, such anti-Tim-3 antibodies can provide options for combinatorial therapies with other checkpoint inhibitors, providing alternatives that may display improved efficacy and toxicity profiles when combined with other therapeutics. Thus, there remains a need to provide antibodies that bind human Tim-3 and inhibit Tim-3's interactions with some of Tim-3's ligands, but not others.

There also remain a need for alternative anti-human Tim-3 antibodies that may be clinically beneficial. In particular, there remains a need for alternative anti-Tim-3 antibodies that specifically bind human Tim-3 and alleviate immune exhaustion such as the failure of the T cell to produce cytokines. There also remains a need for alternative anti-Tim-3 antibodies that specifically bind human Tim-3 and enhance the anti-tumor immune response. There also remains a need for anti-human Tim-3 antibodies that display sufficient potency as a cancer monotherapy.

Anti-Tim-3 antibodies of the present invention can block human Tim-3's binding with human galectin-9 and phosphatidylserine while simultaneously not blocking the binding of human Tim-3 and human CEACAM1. Surprisingly, the anti-Tim-3 antibodies of the present invention enhance T cell responses to tumors as measured by tumor size in established tumor models by blocking the interaction of human Tim-3 with human phosphatidylserine and human galectin-9 while not blocking the interaction of human CEACAM1 with human Tim-3. Surprisingly, certain anti-Tim-3 antibodies of the present invention mediate enhanced T cell responses to a tumor as measured by CD8-positive CD3-positive T cell infiltration or persistence by blocking the interaction of human Tim-3 with human phosphatidylserine and human galectin-9 while not blocking the interaction of human CEACAM1 with human Tim-3.

The present invention provides an antibody that binds human Tim-3 (SEQ ID NO: 1), the antibody comprising HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively.

The present invention provides an antibody that binds human Tim-3, (SEQ ID NO:1), the antibody comprising HCDR1, HCDR2, HCDR3, LCDR1, LCDR2, and LCDR3 wherein:

a) HCDR1 has the amino acid sequence of SEQ ID: 2, HCDR2 has the amino acid sequence of SEQ ID NO: 3, HCDR3 has the amino acid sequence of SEQ ID NO: 4, LCDR1 has the amino acid sequence of SEQ ID NO:5, LCDR2 has the amino acid sequence of SEQ ID NO:6, and LCDR3 has the amino acid sequence of SEQ ID NO:7;

b) HCDR1 has the amino acid sequence of SEQ ID NO:14, HCDR2 has the amino acid sequence of SEQ ID NO:15, HCDR3 has the amino acid sequence of SEQ ID NO:16, LCDR1 has the amino acid sequence of SEQ ID NO:17, LCDR2 has the amino acid sequence of SEQ ID NO:18, and LCDR3 has the amino acid sequence of SEQ ID NO:19; or c) HCDR1 has the amino acid sequence of SEQ ID NO:26, HCDR2 has the amino acid sequence of SEQ ID NO:27, HCDR3 has the amino acid sequence of SEQ ID NO:28, LCDR1 has the amino acid sequence of SEQ ID NO:29, LCDR2 has the amino acid sequence of SEQ ID NO:30, and LCDR3 has the amino acid sequence of SEQ ID NO:31.

The present invention provides an antibody that binds human Tim-3 (SEQ ID NO: 1), the antibody comprising a HCDR1 of SEQ ID NO:2, HCDR2 of SEQ ID NO:3, HCDR3 of SEQ ID NO:4, LCDR1 of SEQ ID NO:5, LCDR2 of SEQ ID NO:6, and LCDR3 of SEQ ID NO:7.

The present invention provides an antibody that binds human Tim-3 (SEQ ID NO: 1), the antibody comprising a HCDR1 of SEQ ID NO:14, HCDR2 of SEQ ID NO:15, HCDR3 of SEQ ID NO:16, LCDR1 of SEQ ID NO:17, LCDR2 of SEQ ID NO:18, and LCDR3 of SEQ ID NO:19.

The present invention provides an antibody that binds human Tim-3 (SEQ ID NO: 1), the antibody comprising a HCDR1 of SEQ ID NO:26, HCDR2 of SEQ ID NO:27, HCDR3 of SEQ ID NO:28, LCDR1 of SEQ ID NO:29, LCDR2 of SEQ ID NO:30, and LCDR3 of SEQ ID NO:31.

The present invention provides an antibody that binds human Tim-3 (SEQ ID NO: 1), the antibody comprising a heavy chain variable region (HCVR) and a light chain variable region (LCVR), wherein: the HCVR has the amino acid sequence given in SEQ ID NO: 8, and the LCVR has the amino acid sequence given in SEQ ID NO: 9; the HCVR has the amino acid sequence given in SEQ ID NO: 20, and the LCVR has the amino acid sequence given in SEQ ID NO: 21; or the HCVR has the amino acid sequence given in SEQ ID NO: 32, and the LCVR has the amino acid sequence given in SEQ ID NO: 33.

The present invention provides an antibody that binds human Tim-3 (SEQ ID NO: 1), the antibody comprising a heavy chain variable region (HCVR) and a light chain variable region (LCVR), wherein: the HCVR has the amino acid sequence given in SEQ ID NO: 8, and the LCVR has the amino acid sequence given in SEQ ID NO: 9.

The present invention provides an antibody that binds human Tim-3 (SEQ ID NO: 1), the antibody comprising a heavy chain variable region (HCVR) and a light chain variable region (LCVR), wherein: the HCVR has the amino acid sequence given in SEQ ID NO: 20, and the LCVR has the amino acid sequence given in SEQ ID NO: 21.

The present invention provides an antibody that binds human Tim-3 (SEQ ID NO: 1), the antibody comprising a heavy chain variable region (HCVR) and a light chain variable region (LCVR), wherein: the HCVR has the amino acid sequence given in SEQ ID NO: 32, and the LCVR has the amino acid sequence given in SEQ ID NO: 33.

The present invention provides an antibody that binds human Tim-3 (SEQ ID NO: 1), the antibody comprising a heavy chain (HC) and a light chain (LC), wherein the HC and the LC have the amino acid sequences given in SEQ ID NOs: 10 and 11, respectively; 22 and 23, respectively; or 34 and 35, respectively.

The present invention provides an antibody that binds human Tim-3 (SEQ ID NO: 1), the antibody comprising a heavy chain (HC) having the amino acid sequence of SEQ ID NO: 10, and a light chain (LC) having the amino acid of SEQ ID NO: 11.

The present invention provides an antibody that binds human Tim-3 (SEQ ID NO: 1), the antibody comprising a heavy chain (HC) having the amino acid sequence of SEQ ID NO: 22 and a light chain (LC) having the amino acid sequence of SEQ ID NO: 23.

The present invention provides an antibody that binds human Tim-3 (SEQ ID NO: 1), the antibody comprising a heavy chain (HC) having the amino acid sequence of SEQ ID NO: 34 and a light chain (LC) having the amino acid sequence of SEQ ID NO: 35.

The present invention provides an anti-human Tim-3 antibody, comprising two heavy chains and two light chains, wherein each heavy chain (HC) has the amino acid sequence of SEQ ID NO: 10 and each light chain (LC) has the amino acid sequence of SEQ ID NO: 11.

The present invention provides an anti-human Tim-3 antibody, comprising two heavy chains and two light chains, wherein each heavy chain (HC) has the amino acid sequence of SEQ ID NO:22 and each light chain (LC) has the amino acid sequence of SEQ ID NO:23.

The present invention provides an anti-human Tim-3 antibody, comprising two heavy chains and two light chains, wherein each heavy chain (HC) has the amino acid sequence of SEQ ID NO: 34 and each light chain (LC) has the amino acid sequence of SEQ ID NO: 35.

The present invention provides an antibody that binds the same epitope on human Tim-3 (SEQ ID NO: 1), as an antibody comprising a HCDR1 of SEQ ID NO:2, HCDR2 of SEQ ID NO:3, HCDR3 of SEQ ID NO:4, LCDR1 of SEQ ID NO:5, LCDR2 of SEQ ID NO:6, and LCDR3 of SEQ ID NO:7. The present invention provides an antibody that binds the same epitope on human Tim-3 (SEQ ID NO: 1), as antibody comprising a heavy chain variable region (HCVR) and a light chain variable region (LCVR), wherein: the HCVR has the amino acid sequence given in SEQ ID NO: 8, and the LCVR has the amino acid sequence given in SEQ ID NO: 9. The present invention provides an antibody that binds the same epitope on human Tim-3 (SEQ ID NO: 1), as an antibody comprising a heavy chain (HC) having the amino acid sequence of SEQ ID NO: 10, and a light chain (LC) having the amino acid of SEQ ID NO: 11.

The present invention provides a monoclonal antibody that binds human Tim-3 (SEQ ID NO:1), wherein said antibody blocks binding of human Tim-3 to human phosphatidylserine, but does not block binding of human Tim-3 to human CEACAM1 (SEQ ID: 39). The present invention provides a monoclonal antibody that binds human Tim-3 (SEQ ID NO:1), wherein said antibody blocks binding of human Tim-3 to human phosphatidylserine and human galectin-9 (SEQ ID: 40), but does not block binding of human Tim-3 to human CEACAM1 (SEQ ID: 39).

The present invention also provides an antibody that binds a human Tim-3 (SEQ ID NO:1) epitope, wherein the antibody contacts residues 50, 55-65, 72, 107, 111, 113-120, and 122 of human Tim-3 (SEQ ID NO:1). The present invention also provides an antibody that binds an epitope on human Tim-3 (SEQ ID NO:1), wherein the antibody contacts residues 50, 55-65, 72, 107, 111, 113-120, and 122 of human Tim-3 (SEQ ID NO:1); wherein the epitope is determined by X-ray crystallography and wherein the residues in contact are within six (6) angstroms or less of the antibody. The present invention also provides an antibody that binds a human Tim-3 (SEQ ID NO:1) epitope, wherein the antibody contacts residues 50, 55-65, 72, 107, 111, 113-120, and 122 of human Tim-3 (SEQ ID NO:1); wherein the epitope is determined by X-ray crystallography and wherein the residues in contact are within six (6) angstroms or less of the antibody; wherein said antibody blocks binding of human Human Tim-3 (SEQ ID NO:1) to human phosphatidylserine and human Tim-3 (SEQ ID NO:1) to human galectin-9 (SEQ ID: 40) (SEQ ID: 40), but does not block binding of human Tim-3 (SEQ ID NO:1) to human CEACAM1 (SEQ ID: 39).

The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive). The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive); wherein the epitope is determined by X-ray crystallography and wherein the residues in contact are within six (6) angstroms or less of the antibody. The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive); wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues.

The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive); and wherein the antibody further contacts at least one residue of the following: 56-61 (inclusive), 107, 119-120 (inclusive), and 122. The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive); and wherein the antibody further contacts at least one residue of the following: 56-61 (inclusive), 107, 119-120 (inclusive), and 122; wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; and wherein the antibody further contacts at least one residue of the following: 56-61 (inclusive), 107, 119-120 (inclusive), and 122.

The present invention provides an antibody that binds an epitope on human Tim-3 (SEQ ID NO:1), wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the antibody further contacts at least one residue of the following: 56-61 (inclusive), 107, 119-120 (inclusive), and 122; wherein the epitope is determined by X-ray crystallography and wherein the residues in contact are within six (6) angstroms or less of the antibody; and wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1), wherein the antibody contacts at least one amino acid residue of the following: 50, 55, 62-65 (inclusive), 72, 111, and 113-118 (inclusive). An antibody that binds human Tim-3 (SEQ ID NO:1), wherein the antibody contacts at least one amino acid residue of the following: 50, 55, 62-65 (inclusive), 72, 111, and 113-118 (inclusive); optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1), wherein the antibody contacts at least one amino acid residue of the following: 50, 55, 62-65 (inclusive), 72, 111, and 113-118 (inclusive); wherein the residues in contact are within six (6) angstroms or less of the antibody, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1), wherein the antibody contacts at least one amino acid residue of the following: 50, 55, 62-65 (inclusive), 72, 111, and 113-118 (inclusive); wherein the residues in contact are within six (6) angstroms or less of the antibody, as determined by X-ray crystallography; wherein the antibody further contacts at least one residue of the following: 56-61 (inclusive), 107, 119-120 (inclusive), and 122; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1), wherein the antibody contacts amino acid residues 50, 55-65, 72, 107, 111, 113-120, and 122. An antibody that binds human Tim-3 (SEQ ID NO:1), wherein the antibody contacts amino acid residues 50, 55-65, 72, 107, 111, 113-120, and 122, as determined by X-ray crystallography. An antibody that binds human Tim-3 (SEQ ID NO:1), wherein the antibody contacts amino acid residues 50, 55-65, 72, 107, 111, 113-120, and 122, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1), wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues.

An antibody that binds human Tim-3 (SEQ ID NO:1), wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1), wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the residues in contact are within six (6) angstroms or less of the antibody, as determined by X-ray crystallography.

An antibody that binds human Tim-3 (SEQ ID NO:1), wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the residues in contact are within six (6) angstroms or less of the antibody, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

The present invention provides an anti-human Tim-3 antibody, wherein the antibody is glycosylated.

The present invention provides a DNA molecule comprising a polynucleotide sequence encoding a polypeptide having the amino acid sequence of SEQ ID NO.10, 22, or 34. The present invention provides a DNA molecule comprising a polynucleotide sequence encoding a polypeptide having the amino acid sequence of SEQ ID NO. 11, 23, or 35. The present invention provides a DNA molecule comprising a pair of polynucleotide sequences encoding two distinct polypeptides having the amino acid sequence of SEQ ID NO. 10 and 11, respectively; 22 and 23, respectively; or 34 and 35, respectively.

The present invention provides a DNA molecule comprising a polynucleotide sequence encoding a polypeptide having the amino acid sequence of SEQ ID NO. 10, 22, or 34, wherein the polynucleotide sequence comprises SEQ ID NO. 12, 24, or 36, respectively. The present invention provides a DNA molecule comprising a polynucleotide sequence encoding a polypeptide having the amino acid sequence of SEQ ID NO. 11, 23, or 35, wherein the polynucleotide sequence comprises SEQ ID NO.13, 25, or 37, respectively.

The present invention provides a mammalian cell capable of expressing an antibody comprising a heavy chain (HC) and a light chain (LC), wherein the HC and the LC have the amino acid sequences given in SEQ ID NOs: 10 and 11, respectively; 22 and 23, respectively; or 34 and 35, respectively.

The present invention provides a mammalian cell capable of expressing an antibody comprising a heavy chain (HC) and a light chain (LC), wherein the HC has the amino acid sequence of SEQ ID NO: 10 and the LC has the amino acid sequence of SEQ ID NO: 11.

The present invention provides a mammalian cell capable of expressing an antibody comprising a heavy chain (HC) and a light chain (LC), wherein the HC has the amino acid sequence of SEQ ID NO: 22 and the LC has the amino acid sequence of SEQ ID NO: 23.

The present invention provides a mammalian cell capable of expressing an antibody comprising a heavy chain (HC) and a light chain (LC), wherein the HC has the amino acid sequence of SEQ ID NO: 34 and the LC has the amino acid sequence of SEQ ID NO: 35.

The present invention provides a process for producing an antibody comprising cultivating a mammalian cell capable of expressing the antibody and recovering the antibody; wherein the antibody comprises a heavy chain and a light chain having the amino acid sequences given in SEQ ID NOs: 10 and 11, respectively; 22 and 23, respectively; or 34 and 35, respectively.

The present invention provides a process for producing an antibody comprising cultivating a mammalian cell capable of expressing the antibody and recovering the antibody; wherein the antibody comprises a heavy chain having the amino acid sequence of SEQ ID NO: 10 and a light chain having the amino acid sequence of SEQ ID NO: 11.

The present invention provides a process for producing an antibody comprising cultivating a mammalian cell capable of expressing the antibody and recovering the antibody; wherein the antibody comprises a heavy chain having the amino acid sequence of SEQ ID NO: 22 and a light chain having the amino acid sequences of SEQ ID NO: 23.

The present invention provides a process for producing an antibody comprising cultivating a mammalian cell capable of expressing the antibody and recovering the antibody; wherein the antibody comprises a heavy chain having the amino acid sequence of SEQ ID NO: 34 and a light chain having the amino acid sequence of SEQ ID NO: 35.

The present invention provides an anti-human Tim-3 antibody disclosed herein produced by a process of the present invention.

The present invention provides a pharmaceutical composition, comprising an anti-human Tim-3 antibody of the present invention, and an acceptable carrier, diluent, or excipient.

The present invention provides a method of treating cancer, comprising administering to a patient in need, thereof an effective amount of an anti-human Tim-3 antibody of the present invention.

In some embodiments, the present invention provides a method of treating cancer, comprising administering to a patient in need, thereof an effective amount of an anti-human Tim-3 antibody, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

In some embodiments, the present invention provides a method of treating cancer, comprising administering to a patient in need, thereof an effective amount of an anti-human Tim-3 antibody, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the the antibody comprises a HCDR1, HCDR2, HCDR3, LCDR1, LCDR2, and LCDR3 consisting of the amino acid sequences shown in SEQ ID NOs: 2, 3, 4, 5, 6, and 7, respectively; 14, 15, 16, 17, 18, and 19, respectively; or 26, 27, 28, 29, 30, and 31, respectively.

In some embodiments, the present invention provides a method of treating cancer, comprising administering to a patient in need, thereof an effective amount of an anti-human Tim-3 antibody, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the the antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9; the HCVR has the amino acid sequence of SEQ ID NO: 20, and the LCVR has the amino acid sequence of SEQ ID NO: 21; or the HCVR has the amino acid sequence of SEQ ID NO: 32, and the LCVR has the amino acid sequence of SEQ ID NO: 33.

In some embodiments, the present invention provides a method of treating cancer, comprising administering to a patient in need, thereof an effective amount of an anti-human Tim-3 antibody, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the the antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides a method of treating cancer, comprising administering to a patient in need, thereof an effective amount of an anti-human Tim-3 antibody of the present invention, wherein the cancer is melanoma. The present invention provides a method of treating cancer, comprising administering to a patient in need, thereof an effective amount of an anti-human Tim-3 antibody of the present invention, wherein the cancer is lung cancer. The present invention provides a method of treating cancer, comprising administering to a patient in need, thereof an effective amount of an anti-human Tim-3 antibody of the present invention, wherein the lung cancer is non-small cell lung cancer. The present invention provides a method of treating cancer, comprising administering to a patient in need, thereof an effective amount of an anti-human Tim-3 antibody of the present invention, wherein the cancer is head and neck cancer. The present invention provides a method of treating cancer, comprising administering to a patient in need, thereof an effective amount of an anti-human Tim-3 antibody of the present invention, wherein the cancer is colorectal cancer. The present invention provides a method of treating cancer, comprising administering to a patient in need, thereof an effective amount of an anti-human Tim-3 antibody of the present invention, wherein the cancer is pancreatic cancer. The present invention provides a method of treating cancer, comprising administering to a patient in need, thereof an effective amount of an anti-human Tim-3 antibody of the present invention, wherein the cancer is gastric cancer. The present invention provides a method of treating cancer, comprising administering to a patient in need, thereof an effective amount of an anti-human Tim-3 antibody of the present invention, wherein the cancer is kidney cancer. The present invention provides a method of treating cancer, comprising administering to a patient in need, thereof an effective amount of an anti-human Tim-3 antibody of the present invention, wherein the cancer is bladder cancer. The present invention provides a method of treating cancer, comprising administering to a patient in need, thereof an effective amount of an anti-human Tim-3 antibody of the present invention, wherein the cancer is prostate cancer. The present invention provides a method of treating cancer, comprising administering to a patient in need, thereof an effective amount of an anti-human Tim-3 antibody of the present invention, wherein the cancer is breast cancer. The present invention provides a method of treating cancer, comprising administering to a patient in need, thereof an effective amount of an anti-human Tim-3 antibody of the present invention, wherein the cancer is ovarian cancer. The present invention provides a method of treating cancer, comprising administering to a patient in need, thereof an effective amount of an anti-human Tim-3 antibody of the present invention, wherein the cancer is esophageal cancer. The present invention provides a method of treating cancer, comprising administering to a patient in need, thereof an effective amount of an anti-human Tim-3 antibody of the present invention, wherein the cancer is soft tissue sarcoma. The present invention provides a method of treating cancer, comprising administering to a patient in need, thereof an effective amount of an anti-human Tim-3 antibody of the present invention, wherein the cancer is liver cancer.

In some embodiments, the methods comprise the administration of an effective amount of an anti-human Tim-3 antibody of the present invention in simultaneous, separate, or sequential combination with one or more chemotherapeutic agents. Non-limiting examples of chemotherapeutic agents include 5-fluorouracil, hydroxyurea, gemcitabine, methotrexate, pemetrexed, doxorubicin, etoposide, cetuximab, carboplatin, cisplatin, cyclophosphamide, melphalan, dacarbazine, taxol, camptothecin, FOLFIRI, docetaxel, daunorubicin, paclitaxel, oxaliplatin, and combinations thereof. In some embodiments, the methods comprise the administration of an effective amount of an anti-human Tim-3 antibody of the present invention in simultaneous, separate, or sequential combination with ionizing radiation.

The present invention provides an anti-human Tim-3 antibody, for use in therapy. The present invention provides an anti-human Tim-3 antibody, for use in therapy; wherein the anti-human Tim-3 antibody binds human Tim-3 (SEQ ID NO: 1) and comprises HCDR1, HCDR2, HCDR3, LCDR1, LCDR2, and LCDR3 consisting of the amino acid sequences shown in SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in therapy; wherein the anti-human Tim-3 antibody binds human Tim-3 (SEQ ID NO: 1) and comprises HCDR1 having the amino acid sequence of SEQ ID NO: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7. The present invention provides an anti-human Tim-3 antibody, for use in therapy; wherein the anti-human Tim-3 antibody binds human Tim-3 and comprises HCDR1 having the amino acid sequence of SEQ ID NO: 14, HCDR2 having the amino acid sequence of SEQ ID NO: 15, HCDR3 having the amino acid sequence of SEQ ID NO: 16, LCDR1 having the amino acid sequence of SEQ ID NO: 17, LCDR2 having the amino acid sequence of SEQ ID NO: 18, and LCDR3 having the amino acid sequence of SEQ ID NO: 19. The present invention provides an anti-human Tim-3 antibody, for use in therapy; wherein the anti-human Tim-3 antibody binds human Tim-3 (SEQ ID NO: 1) and comprises a HCDR1 having the amino acid sequence of SEQ ID NO: 26, HCDR2 having the amino acid sequence of SEQ ID NO: 27, HCDR3 having the amino acid sequence of SEQ ID NO: 28, LCDR1 having the amino acid sequence of SEQ ID NO: 29, LCDR2 having the amino acid sequence of SEQ ID NO: 30, and LCDR3 having the amino acid sequence of SEQ ID NO: 31.

The present invention provides an anti-human Tim-3 antibody, for use in therapy; wherein the anti-human Tim-3 antibody binds human Tim-3 (SEQ ID NO: 1) and comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9; the HCVR has the amino acid sequence of SEQ ID NO: 20, and the LCVR has the amino acid sequence of SEQ ID NO: 21; or the HCVR has the amino acid sequence of SEQ ID NO: 32, and the LCVR has the amino acid sequence of SEQ ID NO: 33. The present invention provides an anti-human Tim-3 antibody, for use in therapy; wherein the anti-human Tim-3 antibody binds human Tim-3 (SEQ ID NO: 1) and comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9. The present invention provides an anti-human Tim-3 antibody, for use in therapy; wherein the anti-human Tim-3 antibody binds human Tim-3 (SEQ ID NO: 1) and comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 20, and the LCVR has the amino acid sequence of SEQ ID NO: 21. The present invention provides an anti-human Tim-3 antibody, for use in therapy; wherein the anti-human Tim-3 antibody binds human Tim-3 (SEQ ID NO: 1) and comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 32, and the LCVR has the amino acid sequence of SEQ ID NO: 33.

The present invention provides an anti-human Tim-3 antibody, for use in therapy; wherein the anti-human Tim-3 antibody binds human Tim-3 (SEQ ID NO: 1) and comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in therapy; wherein the anti-human Tim-3 antibody binds human Tim-3 (SEQ ID NO: 1) and comprises a heavy chain (HC) and a light chain (LC), wherein the HC has the amino acid sequence of SEQ ID NO: 10 and the LC has the amino acid sequence of SEQ ID NO: 11. The present invention provides an anti-human Tim-3 antibody, for use in therapy; wherein the anti-human Tim-3 antibody binds human Tim-3 (SEQ ID NO: 1) and comprises a heavy chain (HC) and a light chain (LC), wherein the HC has the amino acid sequence of SEQ ID NO: 22 and the LC has the amino acid sequence of SEQ ID NO: 23. The present invention provides an anti-human Tim-3 antibody, for use in therapy; wherein the anti-human Tim-3 antibody binds human Tim-3 (SEQ ID NO: 1) and comprises a heavy chain (HC) and a light chain (LC), wherein the HC has the amino acid sequence of SEQ ID NO: 34 and the LC has the amino acid sequence of SEQ ID NO: 35.

The present invention provides an anti-human Tim-3 antibody, for use in the treatment of cancer. The present invention provides an anti-human Tim-3 antibody, for use in the treatment of cancer; wherein the anti-human Tim-3 antibody comprises HCDR1, HCDR2, HCDR3, LCDR1, LCDR2, and LCDR3 consisting of the amino acid sequences shown in SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer; wherein the anti-human Tim-3 antibody comprises HCDR1 having the amino acid sequence of SEQ ID NO: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7. The present invention provides an anti-human Tim-3 antibody, for use in the treatment of cancer; wherein the anti-human Tim-3 antibody comprises HCDR1 having the amino acid sequence of SEQ ID NO: 14, HCDR2 having the amino acid sequence of SEQ ID NO: 15, HCDR3 having the amino acid sequence of SEQ ID NO: 16, LCDR1 having the amino acid sequence of SEQ ID NO:17, LCDR2 having the amino acid sequence of SEQ ID NO: 18, and LCDR3 having the amino acid sequence of SEQ ID NO: 19. The present invention provides an anti-human Tim-3 antibody, for use in the treatment of cancer; wherein the anti-human Tim-3 antibody comprises HCDR1 having the amino acid sequence of SEQ ID NO: 26, HCDR2 having the amino acid sequence of SEQ ID NO: 27, HCDR3 having the amino acid sequence of SEQ ID NO: 28, LCDR1 having the amino acid sequence of SEQ ID NO: 29, LCDR2 having the amino acid sequence of SEQ ID NO: 30, and LCDR3 having the amino acid sequence of SEQ ID NO: 31.

The present invention provides an anti-human Tim-3 antibody, for use in the treatment of cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9; the HCVR has the amino acid sequence of SEQ ID NO: 20, and the LCVR has the amino acid sequence of SEQ ID NO: 21; or the HCVR has the amino acid sequence of SEQ ID NO: 32, and the LCVR has the amino acid sequence of SEQ ID NO: 33. The present invention provides an anti-human Tim-3 antibody, for use in the treatment of cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9. The present invention provides an anti-human Tim-3 antibody, for use in the treatment of cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 20, and the LCVR has the amino acid sequence of SEQ ID NO: 21. The present invention provides an anti-human Tim-3 antibody, for use in the treatment of cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 32, and the LCVR has the amino acid sequence of SEQ ID NO: 33.

The present invention provides an anti-human Tim-3 antibody, for use in the treatment of cancer; wherein the anti-human Tim-3 antibody comprises a heavy chain (HC) and a light chain (LC), wherein the HC and the LC have the amino acid sequences given in SEQ ID NOs: 10 and 11, respectively; 22 and 23, respectively; or 34 and 35, respectively. The present invention provides an anti-human Tim-3 antibody, for use in the treatment of cancer; wherein the anti-human Tim-3 antibody comprises a heavy chain (HC) and a light chain (LC), wherein the HC has the amino acid sequence of SEQ ID NO: 10 and the LC has the amino acid sequence of SEQ ID NO: 11. The present invention provides an anti-human Tim-3 antibody, for use in the treatment of cancer; wherein the anti-human Tim-3 antibody comprises a heavy chain (HC) and a light chain (LC), wherein the HC has the amino acid sequence of SEQ ID NO: 22 and the LC has the amino acid sequence of SEQ ID NO: 23. The present invention provides an anti-human Tim-3 antibody, for use in the treatment of cancer; wherein the anti-human Tim-3 antibody comprises a heavy chain (HC) and a light chain (LC), wherein the HC has the amino acid sequence of SEQ ID NO: 34 and the LC has the amino acid sequence of SEQ ID NO:35.

The present invention provides an anti-human Tim-3 antibody, for use in the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

The present invention provides an anti-human Tim-3 antibody, for use in the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9; the HCVR has the amino acid sequence of SEQ ID NO: 20, and the LCVR has the amino acid sequence of SEQ ID NO: 21; or the HCVR has the amino acid sequence of SEQ ID NO: 32, and the LCVR has the amino acid sequence of SEQ ID NO: 33. The present invention provides an anti-human Tim-3 antibody, for use in the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides an anti-human Tim-3 antibody, for use in the treatment of cancer, wherein the cancer is melanoma. The present invention provides an anti-human Tim-3 antibody, for use in the treatment of cancer, wherein the cancer is lung cancer. The present invention provides an anti-human Tim-3 antibody for use in the treatment of lung cancer, wherein the lung cancer is non-small cell lung cancer. The present invention provides an anti-human Tim-3 antibody, for use in the treatment of cancer, wherein the cancer is head and neck cancer. The present invention provides an anti-human Tim-3 antibody, for use in the treatment of cancer, wherein the cancer is colorectal cancer. The present invention provides an anti-human Tim-3 antibody, for use in the treatment of cancer, wherein the cancer is pancreatic cancer. The present invention provides an anti-human Tim-3 antibody, for use in the treatment of cancer, wherein the cancer is gastric cancer. The present invention provides an anti-human Tim-3 antibody, for use in the treatment of cancer, wherein the cancer is kidney cancer. The present invention provides an anti-human Tim-3 antibody, for use in the treatment of cancer, wherein the cancer is bladder cancer. The present invention provides an anti-human Tim-3 antibody, for use in the treatment of cancer, wherein the cancer is prostate cancer. The present invention provides an anti-human Tim-3 antibody, for use in the treatment of cancer, wherein the cancer is breast cancer. The present invention provides an anti-human Tim-3 antibody, for use in the treatment of cancer, wherein the cancer is ovarian cancer. The present invention provides an anti-human Tim-3 antibody, for use in the treatment of cancer, wherein the cancer is esophageal cancer. The present invention provides an anti-human Tim-3 antibody, for use in the treatment of cancer, wherein the cancer is soft tissue sarcoma. The present invention provides an anti-human Tim-3 antibody, for use in the treatment of cancer, wherein the cancer is liver cancer.

The present invention provides an anti-human Tim-3 antibody, for use in the treatment of cancer, wherein the cancer is melanoma; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is lung cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody for use in the treatment of lung cancer, wherein the lung cancer is non-small cell lung cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is head and neck cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is colorectal cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is pancreatic cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is gastric cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3, for use in the treatment of cancer, wherein the cancer is kidney cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is bladder cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is prostate cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is breast cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is ovarian cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is esophageal cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is soft tissue sarcoma; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody, for use in the treatment of cancer, wherein the cancer is liver cancer; wherein the anti-human Tim-3 antibody comprises a HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively.

The present invention provides an anti-human Tim-3 antibody, for use in the treatment of cancer, wherein the cancer is melanoma; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is lung cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody for use in the treatment of lung cancer, wherein the lung cancer is non-small cell lung cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is head and neck cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is colorectal cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is pancreatic cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is gastric cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3, for use in the treatment of cancer, wherein the cancer is kidney cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is bladder cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is prostate cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is breast cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is ovarian cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is esophageal cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is soft tissue sarcoma; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively. The present invention provides an anti-human Tim-3 antibody, for use in the treatment of cancer, wherein the cancer is liver cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the an anti-human Tim-3 antibody for use in simultaneous, separate, or sequential combination with one or more chemotherapeutic agents.

The present invention provides an anti-human Tim-3 antibody for use in simultaneous, separate, or sequential combination with with one or more chemotherapeutic agents in the treatment of cancer. The present invention provides an anti-human Tim-3 antibody for use in simultaneous, separate, or sequential combination with with one or more chemotherapeutic agents in the treatment of cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides an anti-human Tim-3 antibody for use in simultaneous, separate, or sequential combination with with one or more chemotherapeutic agents in the treatment of cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides an effective amount of an anti-human Tim-3 antibody for use in simultaneous, separate, or sequential combination with ionizing radiation. The present invention provides an effective amount of an anti-human Tim-3 antibody for use in simultaneous, separate, or sequential combination with ionizing radiation in the treatment of cancer. The present invention provides an effective amount of an anti-human Tim-3 antibody for use in simultaneous, separate, or sequential combination with ionizing radiation in the treatment of cancer; wherein the anti-human Tim-3 antibody comprises HCDR1, HCDR2, HCDR3, LCDR1, LCDR2, and LCDR3 consisting of the amino acid sequences shown in SEQ ID NOs: 2, 3, 4, 5, 6, and 7, respectively; 14, 15, 16, 17, 18, and 19, respectively; or 26, 27, 28, 29, 30, and 31, respectively. The present invention provides an effective amount of an anti-human Tim-3 antibody for use in simultaneous, separate, or sequential combination with ionizing radiation in the treatment of cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody for the manufacture of a medicament for the treatment of cancer.

The present invention provides the use of an anti-human Tim-3 antibody for the manufacture of a medicament for the treatment of cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody for the manufacture of a medicament for the treatment of cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively. The present invention provides the use of an anti-human Tim-3 antibody for the manufacture of a medicament for the treatment of cancer; wherein the anti-human Tim-3 antibody comprises HCDR1, HCDR2, HCDR3, LCDR1, LCDR2, and LCDR3 consisting of the amino acid sequences of SEQ ID NOs: 14, 15, 16, 17, 18, and 19, respectively. The present invention provides the use of an anti-human Tim-3 antibody for the manufacture of a medicament for the treatment of cancer; wherein the anti-human Tim-3 antibody comprises HCDR1, HCDR2, HCDR3, LCDR1, LCDR2, and LCDR3 consisting of the amino acid sequences of SEQ ID NOs: 26, 27, 28, 29, 30, and 31, respectively.

The present invention provides the use of an anti-human Tim-3 antibody for the manufacture of a medicament for the treatment of cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9; the HCVR has the amino acid sequence of SEQ ID NO: 20, and the LCVR has the amino acid sequence of SEQ ID NO: 21; or the HCVR has the amino acid sequence of SEQ ID NO: 32, and the LCVR has the amino acid sequence of SEQ ID NO: 33. The present invention provides the use of an anti-human Tim-3 antibody for the manufacture of a medicament for the treatment of cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9. The present invention provides the use of an anti-human Tim-3 antibody for the manufacture of a medicament for the treatment of cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 20, and the LCVR has the amino acid sequence of SEQ ID NO: 21. The present invention provides the use of an anti-human Tim-3 antibody for the manufacture of a medicament for the treatment of cancer; wherein the anti-human Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 32, and the LCVR has the amino acid sequence of SEQ ID NO: 33.

The present invention provides the use of an anti-human Tim-3 antibody for the manufacture of a medicament for the treatment of cancer; wherein the anti-human Tim-3 antibody comprises a heavy chain (HC) and a light chain (LC), wherein the HC and the LC have the amino acid sequences given in SEQ ID NOs: 10 and 11, respectively; 22 and 23, respectively; or 34 and 35, respectively. The present invention provides the use of an anti-human Tim-3 antibody for the manufacture of a medicament for the treatment of cancer; wherein the anti-human Tim-3 antibody comprises a heavy chain (HC) and a light chain (LC), wherein the HC has the amino acid sequence of SEQ ID NO: 10 and the LC has the amino acid sequence of SEQ ID NO: 11. The present invention provides the use of an anti-human Tim-3 antibody for the manufacture of a medicament for the treatment of cancer; wherein the anti-human Tim-3 antibody comprises a heavy chain (HC) and a light chain (LC), wherein the HC has the amino acid sequence of SEQ ID NO: 22 and the LC has the amino acid sequence of SEQ ID NO:23. The present invention provides the use of an anti-human Tim-3 antibody for the manufacture of a medicament for the treatment of cancer; wherein the anti-human Tim-3 antibody comprises a heavy chain (HC) and a light chain (LC), wherein the HC has the amino acid sequence of SEQ ID NO: 34 and the LC has the amino acid sequence of SEQ ID NO: 35.

In a further embodiment, the present invention provides the use of an anti-human Tim-3 antibody for the manufacture of a medicament for the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer. In a further embodiment, the present invention provides the use of an anti-human Tim-3 antibody for the manufacture of a medicament for the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the anti-Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. In a further embodiment, the present invention provides the use of an anti-human Tim-3 antibody for the manufacture of a medicament for the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the anti-Tim-3 antibody comprises a heavy chain (HC) and a light chain (LC), wherein the HC comprises a heavy chain variable region (HCVR) and the LC comprises a light chain variable region (LCVR), wherein: the HCVR has the amino acid sequence of SEQ ID NO: 8, and the LCVR has the amino acid sequence of SEQ ID NO: 9; the HCVR has the amino acid sequence of SEQ ID NO: 20, and the LCVR has the amino acid sequence of SEQ ID NO: 21; or the HCVR has the amino acid sequence of SEQ ID NO: 32, and the LCVR has the amino acid sequence of SEQ ID NO: 33. In a further embodiment, the present invention provides the use of an anti-human Tim-3 antibody for the manufacture of a medicament for the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer; wherein the anti-Tim-3 antibody comprises a heavy chain (HC) and a light chain (LC), wherein the HC and the LC have the amino acid sequences given in SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of melanoma; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of melanoma; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of lung cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of lung cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of non-small cell lung cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of non-small cell lung cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of head and neck cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of head and neck cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of colorectal cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of colorectal cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of pancreatic cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of pancreatic cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of gastric cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of gastric cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of kidney cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of kidney cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of bladder cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of bladder cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of prostate cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of prostate cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of breast cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of breast cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of ovarian cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of ovarian cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of esophageal cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of esophageal cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of soft tissue sarcoma; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of soft tissue sarcoma; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of liver cancer; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of liver cancer; wherein the anti-human Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an anti-human Tim-3 antibody of the present invention in the manufacture of a medicament for the treatment of cancer wherein said medicament is to be administered simultaneously, separately, or sequentially with one or more chemotherapeutic agents. The present invention provides the use of an anti-human Tim-3 antibody of the present invention in the manufacture of a medicament for the treatment of cancer wherein said medicament is to be administered simultaneously, separately, or sequentially with one or more chemotherapeutic agents; wherein the anti-Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an anti-human Tim-3 antibody of the present invention in the manufacture of a medicament for the treatment of cancer wherein said medicament is to be administered simultaneously, separately, or sequentially with one or more chemotherapeutic agents; wherein the anti-Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides the use of an effective amount of an anti-human Tim-3 antibody for the manufacture of a medicament in simultaneous, separate, or sequential combination with ionizing radiation. The present invention provides the use of an effective amount of an anti-human Tim-3 antibody for the manufacture of a medicament in simultaneous, separate, or sequential combination with ionizing radiation; wherein the anti-Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. The present invention provides the use of an effective amount of an anti-human Tim-3 antibody for the manufacture of a medicament in simultaneous, separate, or sequential combination with ionizing radiation; wherein the anti-Tim-3 antibody comprises a heavy chain (HC) and a light chain (LC), wherein the HC and the LC have the amino acid sequences of SEQ ID NOs: 10 and 11, respectively; 22 and 23, respectively; or 34 and 35, respectively.

The present invention provides an anti-human Tim-3 antibody for use in the treatment of cancer, wherein the anti-human Tim-3 antibody blocks binding of human Tim-3 (SEQ ID NO:1) to human galectin-9 (SEQ ID: 40), preferably blocks binding of human Tim-3 (SEQ ID NO:1) to phosphatidylserine, but does not block binding of human Tim-3 (SEQ ID NO:1) to human CEACAM1 (SEQ ID: 39).

The present invention provides a monoclonal antibody that binds human Tim-3 (SEQ ID NO:1) for use in therapy. The present invention provides a monoclonal antibody that binds human Tim-3 (SEQ ID NO:1) for use in the treatment of cancer. The present invention provides a monoclonal antibody that binds human Tim-3 (SEQ ID NO:1) for use in the treatment of cancer, wherein said binding blocks binding of human Tim-3 (SEQ ID NO:1) to human phosphatidylserine, but does not block binding of human Tim-3 (SEQ ID NO:1) to human CEACAM1 (SEQ ID: 39). The present invention provides a monoclonal antibody that binds human Tim-3 (SEQ ID NO:1) for use in the treatment of cancer, wherein said binding blocks binding of human Tim-3 (SEQ ID NO:1) to human phosphatidylserine and human galectin-9 (SEQ ID: 40), but does not block binding of human Tim-3 (SEQ ID NO:1) to human CEACAM1 (SEQ ID: 39).

The present invention provides a monoclonal antibody that binds human Tim-3 (SEQ ID NO:1) for use in simultaneous, separate, or sequential combination with one or more chemotherapeutic agents in the treatment of cancer. The present invention provides a monoclonal antibody that binds human Tim-3 (SEQ ID NO:1) for use in the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer. The present invention provides a monoclonal antibody that binds an epitope of human Tim-3 (SEQ ID NO:1) for use in simultaneous, separate, or sequential combination with ionizing radiation in the treatment of cancer. The present invention provides a monoclonal antibody that binds human Tim-3 (SEQ ID NO:1) for use in the treatment of cancer. The present invention provides a monoclonal antibody that binds human Tim-3 (SEQ ID NO:1) for use in the treatment of cancer, wherein said binding blocks binding of human Tim-3 (SEQ ID NO:1) to human phosphatidylserine, but does not block binding of human Tim-3 (SEQ ID NO:1) to human CEACAM1 (SEQ ID: 39). The present invention provides a monoclonal antibody that binds human Tim-3 (SEQ ID NO:1) (SEQ ID NO:1) for use in the treatment of cancer, wherein said binding blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

The present invention also provides an antibody that binds an epitope on human Tim-3 (SEQ ID NO:1) for use in the treatment of cancer, wherein the antibody contacts residues 50, 55-65, 72, 107, 111, 113-120, and 122. The present invention also provides an antibody that binds an epitope on human Tim-3 (SEQ ID NO:1) for use in the treatment of cancer, wherein the antibody contacts residues 50, 55-65, 72, 107, 111, 113-120, and 122; wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

The present invention provides an antibody that binds an epitope on human Tim-3 (SEQ ID NO:1) for use in the treatment of cancer, wherein the antibody contacts at least one residue of the following: 50, 55, 62-65 (inclusive), 72, 111, and 113-118 (inclusive). The present invention provides an antibody that binds an epitope on human Tim-3 (SEQ ID NO:1) for use in the treatment of cancer, wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues.

The present invention provides an antibody that binds an epitope on human Tim-3 (SEQ ID NO:1) for use in the treatment of cancer, wherein the antibody contacts at least one residue of the following: 50, 55, 62-65 (inclusive), 72, 111, and 113-118 (inclusive); and wherein the antibody further contacts at least one residue of the following: 56-61 (inclusive), 107, 119-120 (inclusive), and 122. The present invention provides an antibody that binds an epitope on human Tim-3 (SEQ ID NO:1) for use in the treatment of cancer, wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; and wherein the antibody further contacts at least one residue of the following: 56-61 (inclusive), 107, 119-120 (inclusive), and 122.

The present invention provides an antibody that binds an epitope on human Tim-3 (SEQ ID NO:1) for use in the treatment of cancer, wherein the antibody contacts at least one residue of the following: 50, 55, 62-65 (inclusive), 72, 111, and 113-118 (inclusive); and wherein the antibody further contacts at least one residue of the following: 56-61 (inclusive), 107, 119-120 (inclusive), and 122. The present invention provides an antibody that binds an epitope on human Tim-3 (SEQ ID NO:1) for use in the treatment of cancer, wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; and wherein the antibody further contacts at least one residue of the following: 56-61 (inclusive), 107, 119-120 (inclusive), and 122.

The present invention provides an antibody that binds an epitope on human Tim-3 (SEQ ID NO:1) for use in the treatment of cancer, wherein the antibody contacts at least one residue of the following: 50, 55, 62-65 (inclusive), 72, 111, and 113-118 (inclusive); wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39); and optionally, wherein the antibody further contacts at least one residue of the following: 56-61 (inclusive), 107, 119-120 (inclusive), and 122. The present invention provides an antibody that binds an epitope on human Tim-3 (SEQ ID NO:1) for use in the treatment of cancer, wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39); and optionally, wherein the antibody further contacts at least one residue of the following: 56-61 (inclusive), 107, 119-120 (inclusive), and 122.

An antibody that binds human Tim-3 (SEQ ID NO:1) for use in the treatment of cancer, wherein the antibody contacts at least one amino acid residue of the following: 50, 55, 62-65 (inclusive), 72, 111, and 113-118 (inclusive). An antibody that binds human Tim-3 (SEQ ID NO:1) for use in the treatment of cancer, wherein the antibody contacts at least one amino acid residue of the following: 50, 55, 62-65 (inclusive), 72, 111, and 113-118 (inclusive); optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for use in the treatment of cancer, wherein the antibody contacts at least one amino acid residue of the following: 50, 55, 62-65 (inclusive), 72, 111, and 113-118 (inclusive); wherein the residues in contact are within six (6) angstroms or less of the antibody, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for use in the treatment of cancer, wherein the antibody contacts at least one amino acid residue of the following: 50, 55, 62-65 (inclusive), 72, 111, and 113-118 (inclusive); wherein the residues in contact are within six (6) angstroms or less of the antibody, as determined by X-ray crystallography; wherein the antibody further contacts at least one residue of the following: 56-61 (inclusive), 107, 119-120 (inclusive), and 122; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for use in the treatment of cancer, wherein the antibody contacts amino acid residues 50, 55-65, 72, 107, 111, 113-120, and 122, as determined by X-ray crystallography. An antibody that binds human Tim-3 (SEQ ID NO:1)) for use in the treatment of cancer, wherein the antibody contacts amino acid residues 50, 55-65, 72, 107, 111, 113-120, and 122, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for use in the treatment of cancer, wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues.

An antibody that binds human Tim-3 (SEQ ID NO:1) for use in the treatment of cancer, wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the residues in contact are within six (6) angstroms or less of the antibody, as determined by X-ray crystallography.

An antibody that binds human Tim-3 (SEQ ID NO:1) for use in the treatment of cancer, wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the residues in contact are within six (6) angstroms or less of the antibody, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for the manufacture of a medicament for the treatment of cancer, wherein the antibody contacts at least one amino acid residue of the following: 50, 55, 62-65 (inclusive), 72, 111, and 113-118 (inclusive). An antibody that binds human Tim-3 (SEQ ID NO:1) for the manufacture of a medicament for the treatment of cancer, wherein the antibody contacts at least one amino acid residue of the following: 50, 55, 62-65 (inclusive), 72, 111, and 113-118 (inclusive); optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for the manufacture of a medicament for the treatment of cancer, wherein the antibody contacts at least one amino acid residue of the following: 50, 55, 62-65 (inclusive), 72, 111, and 113-118 (inclusive); wherein the residues in contact are within six (6) angstroms or less of the antibody, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for the manufacture of a medicament for the treatment of cancer, wherein the antibody contacts at least one amino acid residue of the following: 50, 55, 62-65 (inclusive), 72, 111, and 113-118 (inclusive); wherein the residues in contact are within six (6) angstroms or less of the antibody, as determined by X-ray crystallography; wherein the antibody further contacts at least one residue of the following: 56-61 (inclusive), 107, 119-120 (inclusive), and 122; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for the manufacture of a medicament for the treatment of cancer, wherein the antibody contacts amino acid residues 50, 55-65, 72, 107, 111, 113-120, and 122, as determined by X-ray crystallography. An antibody that binds human Tim-3 (SEQ ID NO:1), wherein the antibody contacts amino acid residues 50, 55-65, 72, 107, 111, 113-120, and 122, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

An antibody that binds human Tim-3 (SEQ ID NO:1) for the manufacture of a medicament for the treatment of cancer, wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues.

An antibody that binds human Tim-3 (SEQ ID NO:1) for the manufacture of a medicament for the treatment of cancer, wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the residues in contact are within six (6) angstroms or less of the antibody, as determined by X-ray crystallography.

An antibody that binds human Tim-3 (SEQ ID NO:1) for the manufacture of a medicament for the treatment of cancer, wherein the antibody contacts at least one amino acid residue of the following: 50, 55, 62-65 (inclusive), 72, 111, and 113-118 (inclusive); wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the residues in contact are within six (6) angstroms or less of the antibody, as determined by X-ray crystallography; optionally, wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

The present invention provides the use of a monoclonal antibody that binds an epitope of human Tim-3 (SEQ ID NO:1) for the manufacture of a medicament for the treatment of cancer. The present invention provides the use of a monoclonal antibody that binds human Tim-3 (SEQ ID NO:1) for the manufacture of a medicament for the treatment of cancer, wherein said binding blocks binding of human Tim-3 (SEQ ID NO:1) to human phosphatidylserine, but does not block binding of human Tim-3 (SEQ ID NO:1) to human CEACAM1 (SEQ ID: 39). The present invention provides the use of a monoclonal antibody that binds an epitope of human Tim-3 (SEQ ID NO:1) for the manufacture of a medicament for the treatment of cancer, wherein said binding blocks the binding of human Tim-3 (SEQ ID NO:1) to human phosphatidylserine and human galectin-9 (SEQ ID: 40), but does not block binding of human Tim-3 (SEQ ID NO:1) to human CEACAM1 (SEQ ID: 39). The present invention provides the use of a monoclonal antibody that binds an epitope of human Tim-3 (SEQ ID NO:1) for the manufacture of a medicament for the treatment of cancer in simultaneous, separate, or sequential combination with one or more chemotherapeutic agents.

The present invention provides the use of a monoclonal antibody that binds an epitope of human Tim-3 (SEQ ID NO:1) for the manufacture of a medicament for the treatment of cancer, wherein the cancer is melanoma, lung cancer, non-small cell lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer. The present invention provides the use of a monoclonal antibody that binds an epitope of human Tim-3 (SEQ ID NO:1) for the manufacture of a medicament for the treatment of cancer in simultaneous, separate, or sequential combination with ionizing radiation.

The present invention provides the use of a monoclonal antibody that binds human Tim-3 (SEQ ID NO:1) for the manufacture of a medicament for the treatment of cancer, wherein said binding blocks binding of human Tim-3 (SEQ ID NO:1) to human phosphatidylserine, but does not block binding of human Tim-3 (SEQ ID NO:1) to human CEACAM1 (SEQ ID: 39). The present invention provides the use of a monoclonal antibody that binds human Tim-3 (SEQ ID NO:1) for the manufacture of a medicament for the treatment of cancer, wherein said binding blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) (SEQ ID NO:1) to human CEACAM1 (SEQ ID: 39). The present invention also provides the use of an antibody that binds an epitope on human Tim-3 (SEQ ID NO:1) for the manufacture of a medicament for the treatment of cancer, wherein the antibody contacts residues 50, 55-65, 72, 107, 111, 113-120, and 122. The present invention also provides the use of an antibody that binds an epitope on human Tim-3 (SEQ ID NO:1) for the manufacture of a medicament for the treatment of cancer, wherein the antibody contacts residues 50, 55-65, 72, 107, 111, 113-120, and 122; wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39).

The present invention provides the use of an antibody that binds an epitope on human Tim-3 (SEQ ID NO:1) for the manufacture of a medicament for the treatment of cancer, wherein the antibody contacts at least one residue of the following: 50, 55, 62-65 (inclusive), 72, 111, and 113-118 (inclusive). The present invention provides the use of an antibody that binds an epitope on human Tim-3 (SEQ ID NO:1) for the manufacture of a medicament for the treatment of cancer, wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues.

The present invention provides the use of an antibody that binds an epitope on human Tim-3 (SEQ ID NO:1) for the manufacture of a medicament for the treatment of cancer, wherein the antibody contacts at least one residue of the following: 50, 55, 62-65 (inclusive), 72, 111, and 113-118 (inclusive); and wherein the antibody further contacts at least one residue of the following: 56-61 (inclusive), 107, 119-120 (inclusive), and 122. The present invention provides the use of an antibody that binds an epitope on human Tim-3 (SEQ ID NO:1) for the manufacture of a medicament for the treatment of cancer, wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; and wherein the antibody further contacts at least one residue of the following: 56-61 (inclusive), 107, 119-120 (inclusive), and 122.

The present invention provides the use of an antibody that binds an epitope on human Tim-3 (SEQ ID NO:1) for the manufacture of a medicament for the treatment of cancer, wherein the antibody contacts at least one residue of the following: 50, 55, 62-65 (inclusive), 72, 111, and 113-118 (inclusive); wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39); and optionally, wherein the antibody further contacts at least one residue of the following: 56-61 (inclusive), 107, 119-120 (inclusive), and 122. The present invention provides the use of an antibody that binds an epitope on human Tim-3 (SEQ ID NO:1) for the manufacture of a medicament for the treatment of cancer, wherein the antibody contacts at least one residue of the following: 50, 55, 62-65 (inclusive), 72, 111, and 113-118 (inclusive), wherein the antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the epitope is determined by X-ray crystallography and wherein the residues in contact are within six (6) angstroms or less of the antibody; wherein said antibody blocks binding of human Tim-3 (SEQ ID NO:1) to human phosphatidylserine and human Tim-3 (SEQ ID NO:1) to human galectin-9 (SEQ ID: 40), but does not block binding of human Tim-3 (SEQ ID NO:1) to human CEACAM1 (SEQ ID: 39); and optionally, wherein the antibody further contacts at least one residue of the following: 56-61 (inclusive), 107, 119-120 (inclusive), and 122.

A pharmaceutical composition for the treatment of cancer, comprising an antibody that binds human Tim-3 (SEQ ID NO:1), the antibody comprising HCDR1, HCDR2, HCDR3, LCDR1, LCDR2, and LCDR3 wherein: HCDR1 has the amino acid sequence of SEQ ID: 2, HCDR2 has the amino acid sequence of SEQ ID NO: 3, HCDR3 has the amino acid sequence of SEQ ID NO: 4, LCDR1 has the amino acid sequence of SEQ ID NO:5, LCDR2 has the amino acid sequence of SEQ ID NO:6, and LCDR3 has the amino acid sequence of SEQ ID NO:7; HCDR1 has the amino acid sequence of SEQ ID NO:14, HCDR2 has the amino acid sequence of SEQ ID NO:15, HCDR3 has the amino acid sequence of SEQ ID NO:16, LCDR1 has the amino acid sequence of SEQ ID NO:17, LCDR2 has the amino acid sequence of SEQ ID NO:18, and LCDR3 has the amino acid sequence of SEQ ID NO:19; or HCDR1 has the amino acid sequence of SEQ ID NO:26, HCDR2 has the amino acid sequence of SEQ ID NO:27, HCDR3 has the amino acid sequence of SEQ ID NO:28, LCDR1 has the amino acid sequence of SEQ ID NO:29, LCDR2 has the amino acid sequence of SEQ ID NO:30, and LCDR3 has the amino acid sequence of SEQ ID NO:31.

A pharmaceutical composition for the treatment of cancer, comprising an antibody that binds human Tim-3 (SEQ ID NO:1), the antibody comprising a heavy chain variable region (HCVR) and a light chain variable region (LCVR), wherein: the HCVR has the amino acid sequence of SEQ ID NO: 8, and the LCVR has the amino acid sequence of SEQ ID NO: 9; the HCVR has the amino acid sequence of SEQ ID NO: 20, and the LCVR has the amino acid sequence of SEQ ID NO: 21; or the HCVR has the amino acid sequence of SEQ ID NO: 32, and the LCVR has the amino acid sequence of SEQ ID NO: 33.

A pharmaceutical composition for the treatment of cancer, comprising an antibody that binds human Tim-3 (SEQ ID NO:1), the antibody comprising a heavy chain (HC) and a light chain (LC), wherein: the HC has the amino acid sequence of SEQ ID NO: 10 and the LC has the amino acid sequence of SEQ ID NO: 11; the HC has the amino acid sequence of SEQ ID NO: 22 and the LC has the amino acid sequence of SEQ ID NO: 23; or the HC has the amino acid sequence of SEQ ID NO: 34 and the LC has the amino acid sequence of SEQ ID NO: 35.

A pharmaceutical composition for the treatment of cancer, comprising an antibody that binds human Tim-3 (SEQ ID NO:1), the antibody comprising a heavy chain (HC) and a light chain (LC), wherein: the HC has the amino acid sequence of SEQ ID NO: 10 and the LC has the amino acid sequence of SEQ ID NO: 11; the HC has the amino acid sequence of SEQ ID NO: 22 and the LC has the amino acid sequence of SEQ ID NO: 23; or the HC has the amino acid sequence of SEQ ID NO: 34 and the LC has the amino acid sequence of SEQ ID NO: 35; wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

A pharmaceutical composition for the treatment of cancer, comprising an antibody that binds human Tim-3 (SEQ ID NO:1), wherein the antibody contacts residues 50, 55-65, 72, 107, 111, 113-120, and 122 of human Tim-3 (SEQ ID NO:1); wherein the residues in contact are within six (6) angstroms or less of the antibody, as determined by X-ray crystallography.

A pharmaceutical composition for the treatment of cancer, comprising an antibody that binds human Tim-3 (SEQ ID NO:1), wherein the antibody contacts residues 50, 55-65, 72, 107, 111, 113-120, and 122 of human Tim-3 (SEQ ID NO:1); wherein the residues in contact are within six (6) angstroms or less of the antibody, as determined by X-ray crystallography; wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

In some embodiments, a method of evaluating the efficacy of an anti-human Tim-3 (SEQ ID NO:1) antibody is provided, the method comprising (a) combining a murine T cell hybridoma expressing human Tim-3 (SEQ ID NO:1), a murine antigen-presenting cell, a peptide recognized by the murine T cell hybridoma, and an anti-human Tim-3 antibody, and (b) measuring murine cytokine production. In some embodiments, a method of evaluating the efficacy of an anti-human Tim-3 antibody is provided, the method comprising (a) combining a murine T cell hybridoma expressing human Tim-3 (SEQ ID NO:1), a murine antigen presenting cell, a peptide recognized by the murine T cell hybridoma, and an anti-human Tim-3 antibody, and (b) measuring murine cytokine production; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively.

In some embodiments, a method of evaluating the efficacy of an anti-human Tim-3 (SEQ ID NO:1) antibody is provided, the method comprising (a) combining a murine T cell hybridoma expressing human Tim-3 (SEQ ID NO:1), a murine antigen-presenting cell, a peptide recognized by the murine T cell hybridoma, and an anti-human Tim-3 antibody, and (b) measuring murine cytokine production; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively; wherein the peptide recognized by the murine T cell hybridoma is ISQAVHAAHAEINEAGR (SEQ ID NO: 38); wherein the murine cytokine is IL-2, interferon-gamma, TNF-alpha, or combinations thereof.

In some embodiments, a method of evaluating the efficacy of an anti-human Tim-3 antibody is provided, the method comprising (a) combining a murine T cell hybridoma expressing human Tim-3 (SEQ ID NO:1), a murine antigen-presenting cell, a peptide recognized by the murine T cell hybridoma, and an anti-human Tim-3 antibody, and (b) measuring murine cytokine production; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively; wherein the peptide recognized by the murine T cell hybridoma is ISQAVHAAHAEINEAGR (SEQ ID NO: 38); wherein the murine cytokine is IL-2, interferon-gamma, TNF-alpha, or combinations thereof; wherein the murine cytokine production is measured by enzyme-linked immunospot assay, enzyme-linked immunosorbent assay, or flow cytometry; and wherein the murine antigen presenting cell is an A20 cell.

In some embodiments, a method of evaluating the efficacy of an anti-human Tim-3 antibody is provided, the method comprising (a) combining a murine T cell hybridoma expressing human Tim-3 (SEQ ID NO:1) and an anti-human Tim-3 antibody, and (b) measuring the binding of the anti-human Tim-3 antibody to the murine T cell hybrioma expressing Tim-3; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively. In some embodiments, a method of evaluating the efficacy of an anti-human Tim-3 antibody is provided, the method comprising (a) combining a murine T cell hybridoma expressing human Tim-3 (SEQ ID NO:1) and an anti-human Tim-3 antibody, and (b) measuring the binding of the anti-human Tim-3 antibody to the murine T cell hybrioma expressing Tim-3; wherein the anti-human Tim-3 antibody comprises HCDR1, HCDR2, HCDR3, LCDR1, LCDR2, and LCDR3 consisting of the amino acid sequences of SEQ ID NOs: 2, 3, 4, 5, 6, and 7, respectively; 14, 15, 16, 17, 18, and 19, respectively; or 26, 27, 28, 29, 30, and 31, respectively; wherein the binding of the anti-human Tim-3 antibody is measured by flow cytometry.

The murine antigen presenting preferably is syngeneic with the murine T cell hybridoma prior to introducing the human Tim-3 gene into the murine T cell hybridoma. The murine antigen presenting cells are murine cells that express the major histocompatibility complex II gene(s); non-limiting examples of which include I-A$^d$. Non-limiting examples of murine antigen presenting cells include B cells, dendritic cells, and monocytes/macrophages. The murine antigen present cell can be a primary cell or a cell line, a non-limiting example of which includes an A20 cell (ATCC® TIB-208™; a murine B lymphocyte cell line derived from a BALB/cAnN mouse). Non-limiting examples of murine T cell hybridomas include DO11.10 T cell hybridomas as described by Shimonkevitz et al., Antigen Recognition by H-2-Restricted T cells, Journal of Immunology 133(4), pp. 2067-2074. In some embodiments, the murine cytokine production is measured at the RNA level by methods including, but not limited to real-time PCR, multiplex real time PCR, and PCR. In some embodiments, the murine cytokines include other cytokines, non-limiting examples of which include IL-10, TNF-beta/LT-alpha, IL-3, IL-4, IL-5, IL-6, IL-13, IL-17A, IL-17E, IL-17F, IL-17AF heterodimer, IL-21, IL-22, IL-26, IL-31, GM-CSF, and MIP-3alpha.

An antibody of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in an antibody of the present invention.

The antibody of the present invention is an IgG type antibody and has "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, certain anti-Tim-3 antibodies described herein contain an Fc portion that is derived from human IgG$_1$. IgG1 is well known to bind to the proteins of the Fc-gamma receptor family (FcγR) as well as C1q. Interaction with these receptors can induce antibody-dependent cell cytotoxicity (ADCC) and complement-dependent cytotoxicity (CDC). Therefore, optionally, certain anti-Tim-3 antibodies described herein are a fully human monoclonal antibody lacking Fc effector function (IgG1, Fc-null). To achieve an Fc-null IgG1 antibody, selective mutagenesis of residues is necessary within the CH2 region of its IgG1 Fc region Amino acid substitutions L234A, L235E, and G237A are introduced into IgG1 Fc to reduce binding to FcγRI, FcγRIIa, and FcγRIII, and substitutions A330S and P331S are introduced to reduce C1q-mediated complement fixation. To reduce the potential induction of an immune response when dosed in humans, certain amino acids may require back-mutations to match antibody germline sequences.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. There are currently three systems of CDR assignments for antibodies that are used for sequence delineation. The North CDR definition (North et al., "A New Clustering of Antibody CDR Loop Conformations", Journal of Molecular Biology, 406, 228-256 (2011)) is based on affinity propagation clustering with a large number of crystal structures. For the purposes of the present invention, the North CDR definitions are used.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a human kappa or lambda constant region. Preferably for antibodies of the present invention, the light chain constant region is a human kappa constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody of the present invention may readily be produced in mammalian cells, non-limiting examples of which includes CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice*, 3rd Edition, Springer, NY (1994).

In other embodiments of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes (e.g., subcutaneous and intravenous). An antibody of the present invention may be administered to a patient along with pharmaceutically acceptable carriers, diluents, or excipients in single or multiple doses. Pharmaceutical compositions of the present invention can be prepared by methods well known in the art (e.g., *Remington: The Science and Practice of Pharmacy*, 22$^{nd}$ ed. (2012), A. Loyd et al., Pharmaceutical Press) and comprise an antibody, as disclosed herein, and one or more pharmaceutically acceptable carriers, diluents, or excipients.

Dosage regimens may be adjusted to provide the optimum desired response (e.g., a therapeutic effect). Treatment dosages may be titrated to optimize safety and efficacy. Dosing schedules, for intravenous (i.v.) or non-intravenous administration, localized or systemic, or combinations, thereof will typically range from a single bolus dosage or continuous infusion to multiple administrations per day (e.g., every 4-6 hours), or as indicated by the treating physician and the patient's condition.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

WINN Assay

The antibodies of the present invention can be tested for in vivo immunomodulatory activity with the WINN assay. In the WINN assay, human NSCLC tumor cells NCI-H292 and human immune cells (allogeneic) are mixed and co-implanted into an immunodeficient mouse, and then followed by dosing with an immunomodulatory agent. The ability of the immunomodulatory agent to inhibit or delay tumor formation or support intra-tumroal persistence can be assessed as follows.

On day 0, NSG mice from Jackson Laboratories (7 weeks of age, female, in groups of 8-10 mice) are implanted into the flank subcutaneously with either $2 \times 10^6$ H292 cells, or a mixture of $2 \times 10^6$ H292 cells and $1 \times 10^6$ human PBMCs in HBSS (0.2 ml total volume). Starting on Day 0, mice are treated with an i.p. injection of control human IgG at 10 mg/kg or Antibody A at 1 mg/kg or 10 mg/kg, one time per week for six weeks. Animal well-being and behavior, including grooming and ambulation, are monitored at least twice per week.

Tumor sections from the model can be analyzed for CD3-positive and CD8-positive T cell persistence by measuring the presence of CD3-positive and CD8-positive T cells by staining for CD3 and CD8 and analyzing with the Aperio ScanScope™. The IHC Nuclear Image Analysis macro detects nuclear staining for a target chromogen for the individual cells in those regions that are chosen by the user and quantifies their intensities. Three to five annotations are made from viable tumor area and used in adjusting the parameters until the algorithm results generate consistent cell identification. The macro is then saved and the slides logged in for analysis. The % CD3-positive and CD8-positive cells as a percent of the total number of cells are calculated by the Aperio software.

In experiments performed essentially as described in this WINN assay, by IHC analysis, mice co-implanted with NCI-H292 tumors and PBMCs and dosed with Antibody A at 10 mg/kg results in a significant increase (30%) of human CD3-positive CD8-positive intratumoral T cells as compared to mice co-implanted with NCI-H292 tumors and PBMCs and treated with the control IgG (6.5%) (P=0.03).

Established Human Tumor Xenograft Model in NSG Mice Humanized with Primary Human T Cells The efficacy of the antibodies of the present invention can be tested in the NCI-HCC827 human NSCLC (non-small cell lung cancer) xenograft model to assess the ability to delay or destroy established tumors in the model. On day 0, $1 \times 10^7$ NCI-HCC827 cells are implanted subcutaneously into the flank of NSG mice (7 weeks of age, female, 8 mice per group). When tumors reach a volume of ~400 mm³ (~days 30-32), the mice are infused (i.v.) with $2.5 \times 10^6$ previously expanded human T cells. Previously expanded human T cells are generated by isolating human T cells from whole blood and expanding using Dynabeads® Human T-Activator CD3/CD28 for 10 days. Previously expanded human T cells may be cryopreserved for later use. One day after T cell infusion, mice are dosed at 10 mg/kg by weekly (4 total doses) i.p. injection with human IgG or Antibody A. Animal well-being and behavior, including grooming and ambulation are monitored at least twice per week.

Body weight and tumor volume are measured twice a week. Tumor volumes were measured twice per week starting on day 4 post-cell implantation using electronic calipers as described above. Tumor Volume (mm³)=π/6*Length*Width². The antitumor efficacy is expressed as T/C ratio in percent and calculated as summarized below: % T/C is calculated by the formula 100 ΔT/ΔC if ΔT>0 of the geometric mean values. ΔT=mean tumor volume of the drug-treated group on the final day of the study−mean tumor volume of the drug-treated group on initial day of dosing; ΔC=mean tumor volume of the control group on the final day of the study−mean tumor volume of the control group on initial day of dosing. Additionally, % Regression is calculated using the formula=100×ΔT/T$_{initial}$ if ΔT<0. Animals with no measurable tumors are considered as Complete Responders (CR) and tumors with >50% regressions are Partial Responders (PR).

In experiments performed essentially as described above, treatment with Antibody A (anti-human Tim-3) significantly inhibits tumor growth in the humanized NSG mice, compared to treatment with human IgG (Table 1). On day 76, treatment with Antibody A results in a T/C=2%. On day 110, Antibody A treatment results in a 3/8 CR.

TABLE 1

Tumor volume (mm³) in the NCI-HCC827 human NSCLC xenograft model

| Day | Human IgG Control Mean | SEM | Antibody A Mean | SEM |
|---|---|---|---|---|
| 21 | 152 | 13 | 164 | 85 |
| 28 | 289 | 24 | 309 | 160 |
| 30 | 332 | 28 | 358 | 186 |
| 34 | 388 | 32 | 403 | 209 |
| 36 | 414 | 34 | 505 | 262 |
| 40 | 706 | 59 | 628 | 326 |
| 43 | 752 | 62 | 733 | 380 |
| 47 | 858 | 71 | 763 | 396 |
| 50 | 932 | 77 | 747 | 387 |
| 55 | 982 | 81 | 807 | 418 |
| 57 | 1212 | 100 | 843 | 437 |
| 62 | 1324 | 110 | 553 | 287 |
| 65 | 1524 | 126 | 726 | 376 |
| 69 | 1492 | 124 | 602 | 312 |
| 72 | 1827 | 151 | 539 | 279 |
| 76 | 2030 | 168 | 375 | 196 |
| 79 | | | 375 | 196 |
| 83 | | | 414 | 218 |
| 85 | | | 331 | 175 |
| 90 | | | 192 | 103 |
| 93 | | | 235 | 128 |
| 97 | | | 173 | 95 |
| 100 | | | 118 | 65 |
| 103 | | | 125 | 69 |
| 106 | | | 120 | 67 |
| 110 | | | 131 | 73 |

Mixed Lymphocyte Reaction

The function of blocking Tim-3 signals by antibodies of the present invention may be evaluated by measuring the release of cytokines during T cell activation. The levels of certain cytokines, such as IFN-γ, are expected to increase if T cell activation is promoted by treatment with antibodies of the present invention.

CD14⁺ monocytes are isolated by negative selection from fresh human PBMC obtained from a healthy donor (AllCells) using human monocyte isolation kit II (Miltennyi Biotec). Human monocyte-derived dendritic cells are generated by culturing the CD14⁺ monocytes in complete RPMI-1640 medium in the presence of 62.5 ng/ml hGM-CSF and 20 ng/ml hIL-4 for 7 days. CD4⁺ T cells are purified from fresh human PBMC of a different healthy donor (AllCells) by negative selection using the CD4 T cell isolation kit (Miltenyi). The two types of cells are then mixed in individual wells of a 96-well plate with 100 μl complete AIM-V medium containing $1 \times 10^5$ CD4⁺ T cells and $2 \times 10^4$ immature DC per well. 100 μl complete AIM-V medium is added containing 100 nM human IgG1 or Antibody A in 6 replicates. After incubation for 3 days at 37° C. at 5% CO₂, supernatants are harvested and measured for human IFN-γ with an ELISA kit (R&D Systems). An unpaired t-test is used to compare groups.

In experiments performed essentially as described above, the addition of Antibody A significantly increases the secretion of IFN-γ as compared to the addition of control human IgG1 (3,036±367 vs. 1,644±261 pg/mL of hIFN-γ; p=0.0384).

ELISA Analysis: Antibody A Binds to Recombinant Tim-3

The ability for antibodies of the present invention to bind human Tim-3 can be measured with an ELISA assay. For the Tim-3 binding assay, a 96-well plate (Nunc) is coated with human Tim-3-Fc (R&D Systems) overnight at 4° C. Wells are blocked for 2 h with blocking buffer (PBS containing 3% bovine serum albumin). Wells are washed three times with PBS containing 0.1% Tween-20. Antibody A or control IgG (100 μl) is then added and incubated at room temperature for 1 h. After washing, the plate is incubated with 100 μl of goat anti-human IgG F(ab')2-HRP conjugate (Jackson Immuno Research) at room temperature for 1 h. The plates are washed and then incubated with 100 μl of 3,3',5,5'-tetramethylbenzidine. The absorbance at 450 nm is read on a microplate reader. The half maximal effective concentration (EC50) is calculated using GraphPad Prism 6 software.

In experiments performed essentially as described above, Antibody A binds human Tim-3 with an EC50 of $2.07 \times 10^{-11}$ M.

Flow Cytometric Analysis: Antibody A Binds to Cell Surface Tim-3

The ability for antibodies of the present invention to bind to cell surface human Tim-3 can be measured with a flow cytometric assay. Tim-3 DO11.10 cells, a human Tim-3 expressing DO11.10 cell line, are used for this assay.

Tim-3 DO11.10 cells can be obtained as follows. Full-length Tim-3 gene can be purchased from Origene Technologies, Inc. and cloned into a pLVX-IRES-Neo lentivirus vector from Clonetech Laboraties, Inc. using PCR. Lenti-X™ system from Clonetech Laboraties, Inc. is used to generate high titers of recombinant, replication-incompetent virions. The virions are either used to infect the target cells immediately or are aliquoted and frozen at −80 until use. The murine T cell hybridoma, DO11.10 cell line, can be obtained from the National Jewish Health®. The DO11.10s are cultured and maintained according to a protocol accompanying this cell line. On day 0, DO11.10 cells are counted and spun down to remove culture media. Cell pellets are mixed with virions containing the human TIM-3 gene or vector control and incubated at 37° C. for 24 hours. Polybrene is added when mixing cells and virions until a final concentration of 8 ug/ml is achieved. After 24 hours, DO11.10 cells are pelleted again and resuspended in fresh culture media and incubated at 37° C. for 3 days. Next, the DO11.10 cells are pelleted every 3 days and resuspended in selection media containing 1 mg/ml Geneticin® to select stably transduced cells. Tim-3 expression is monitored by flow cytometry using antibodies obtained from R&D Systems. After 2 to 3 weeks in selection media, the resulting Tim-3 expressing DO11.10 cells are sorted to establish a single cell clone.

DO11.10 and Tim-3 DO11.10 cells are added to a 96 well V-bottom plate at $1.\times10^5$ cells per well (100 μl/well) in staining buffer (DPBS containing 3% BSA). Cells are Fc blocked on ice for 1 hour in staining buffer with 30 μg/mL human IgG. Antibody A or control human IgG is labelled with A488 (Molecular Probes®) and 12 point titrations (1:3 serial dilutions) of both antibodies are prepared in staining buffer with a starting concentration of 66.7 nM. Labelled antibodies are added to the cells and incubated for 1 hour at 4° C. in the dark. Cells are washed two times with PBS by spinning for 5 min at 1200 RPM and decanting the supernatant. Live/Dead cell dye 7-AAD (1:1000 in PBS) is added to each well at 3 μl/well and cells are incubated for 15 min on ice. Cells are washed two times with PBS and resuspended in 100 μl DPBS containing 0.5% BSA and analyzed on an Intellictye iQue. All stainings are done in triplicate. Data are analyzed with FlowJo software to identify populations of live cells and determine the median fluorescence intensity of each sample using the AF488 (FL1) detection channel. The individual MFI (i.e. mean fluorescence intensity) values are placed into GraphPad Prism software to generate concentration response curves from which EC50 values are extrapolated.

In experiments performed essentially as described above, Antibody A binds to cellular bound human Tim-3 on Tim-3 DO11.10 cells in a dose dependent manner with an EC50 value of 0.09 nM.

Flow Cytometric Analysis: Antibody A Blocks the Interaction of Phosphatidylserine with Human Tim-3

The ability for certain antibodies of the present invention to block phosphatidylserine binding to Tim-3 can be measured by FACS analysis. For this receptor-ligand blocking assay, $1\times10^6$/ml of DO11.10 cells are treated with 12 μM camptothecin (Sigma®) for 3 hours at 37° C. to induce apoptosis. FITC-Annexin V (Becton Dickinson®) is used as a positive control to detect the existence of phosphatidylserine. Biotinylated hTIM-3-Fc binds strongly to camptothecin-treated cells but does not bind to non-treated cells. Camptothecin-treated cells are washed with cold PBS and resuspended in binding buffer (Becton Dicknson®) at $1\times10^6$ cells/ml. Fc receptors are blocked by adding 50 μg/ml mouse IgG and rat IgG to the cells and incubating at room temperature for 30 min. 6 point titrations (1:3 serial dilutions) of Antibody A are prepared in binding buffer with a starting concentration of 90 nM and added to 1 ml of cells and cells are then incubated for 60 min at room temperature. hTIM-3-Fc Biotin is then added at 0.05 μg/well to the appropriate samples in a 200 μl volume and incubated for 30 min at room temperature. Cells are then washed twice with binding buffer by centrifugation at 1200 RPM for 5 min 2.4 μl/well of a streptavidin-FITC (Biolegend®) containing solution (1:10 dilution in DPBS) and 5 μl/well of propidium iodide are added to each well and incubated for 30 min at room temperature in the dark. Cells are washed twice with binding buffer and resuspended in 100 μl of PBS. Samples are read on the IntelliCyt iQue Flow Cytometer and Data were analyzed with FlowJo software. The individual MFI (i.e. mean fluorescence intensity) values are placed into GraphPad Prism software to generate concentration response curves from which IC50 values are extrapolated.

In experiments performed essentially as described above, Antibody A blocks the interaction of human Tim-3 with phosphatidylserine in a dose-dependent manner with an IC50 value of 0.32 nM and as further illustrated in Table 2.

TABLE 2

|  | Untreated DO11.10 + hTIM-3-Fc Biotin | Camptothecin-treated DO11.10 + hTIM-3-Fc Biotin | | | | | | |
| --- | --- | --- | --- | --- | --- | --- | --- | --- |
| Antiboby A (nM) | 0 | 90 | 30 | 10 | 3.3 | 1.1 | 0.37 | 0 |
| MFI | 1747 | 1815 | 19655 | 32574 | 52885 | 96566 | 197146 | 214044 |

Galectin-9 Blocking Assay: Antibody A Blocks the Interaction of Human Galectin-9 with Human Tim-3

The ability for antibodies of the present invention to block human galectin-9 binding to human Tim-3 can be measured as follows. For this receptor-ligand blocking assay, a 96-well streptavidin-coated MSD plate (Meso Scale Diagnostics) is blocked for 2 hours with 150 μl blocking buffer (PBST containing 5% bovine serum albumin). Wells are washed three times with 200 μl PBS containing 0.2% Tween-20. Recombinant human galectin-9 (R&D Systems) is biotinylated using EZ-Link™ biotin (Thermo Scientific™) and then 25 μl of 0.21 μg/ml of the human recombinant galectin-9-biotin is then added and incubated at room temperature for 2 hours. Plates are washed three times with PBS containing 0.2% Tween-20. Human Tim-3-Fc protein (R&D Systems)

is ruthinylated using sulfo-tag NHS-ester reagent (Meso Scale Discovery®) and a small aliquot is stored at −80 until use. Antibodies are serially diluted (starting at 13.5 μg/ml) and 50 μl of each antibody combined with 50 μl of diluted hTim-3-Fc-ruth at 0.05 μg/ml and incubated for 1 hour at room temperature. 50 μl of each combination is then added to the plate and incubated for 1.5 hours at room temperature. Plates are washed three times with PBS containing 0.2% Tween-20. 150 μl of 1× read buffer (Meso Scale Diagnostics) is then added to each well of the plate and the plate is read on a Sector Imager 2400 (Meso Scale Diagnostics).

In experiments performed essentially as described above, Antibody A blocks the interaction of human Tim-3 with human galectin-9 with an IC50 value of 5.6 nM as compared to control a polyclonal anti-human Tim-3 antibody (R&D Systems) with an IC50 value of 7.8 nM. However, The polyclonal anti-human Tim-3 antibody can block up to 100% human Tim-3's interactions with human galectin-9 while Antibody A only achieve partial blockage in this assay. CEACAM-1 Blocking Assay: Antibody A does not Block the Interaction of Human CEACAM1 with Human Tim-3

The ability for antibodies of the present invention to block human CEACAM1 binding to human Tim-3 can be measured as follows. For this receptor-ligand blocking assay, a 96-well Immulon 4HBX plate (Thermo Scientific) is coated with 100 μl/well of 1 ug/ml human Tim-3-Fc at 4° C. The plate is washed three times with PBS containing 0.2% Tween-20 and blocked with 200 μl/well of PBS with 3% BSA for 1 hour at room temperature. Blocking buffer is then removed and 50 μl of titrated Abs (including polyclonal anti-human Tim-3, R&D Systems, Antibody A, and control human IgG), starting at 600 nM are added to the plate and incubated for 1 hour at room temperature. 50 μl of 20 μg/ml of CEACAM1 (BIOTANG) is then added directly to the wells and incubated for 1 hour at room temperature (final concentration of antibody is 300 nM and of CEACAM1 is 10 μg/ml). The plate is washed three times with PBS containing 0.2% Tween-20 and 100 μl of 0.2 μg/ml of biotinylated human CEACAM1 antibody (R&D Systems) is added and then incubated for 1 hour at room temperature. The plate is washed three times with PBS containing 0.2% Tween-20 and then 100 μl of streptavidin peroxidase (Jackson ImmunoResearch Laboratories) is added and then incubated for 1 hour at room temperature. The plate is washed six times with PBS containing 0.2% Tween-20 and developed using 100 μl/well of a 1:1 TMB substrate solution A and B (KPL) for 10 min at room temperature. The reaction is then stopped with 100 μl/well of 0.1N $H_2SO_4$ and the plate is read on a SpectraMax® plate reader at 450 nm.

In experiments performed essentially as described above, Antibody A does not significantly block the binding of CEACAM1 to human Tim-3, as illustrated in Table 3 below.

Epitope

A Fab for Antibody A is generated by by enzymatically clipping Antibody A with immobilized (agarose resin) papain (ThermoFisher Scientific) followed by a standard ProA column (GE Healthcare Life Sciences) purification to pull out the free, soluble Fc and the unclipped IgG. Flow through containing the Fab is collected to concentrate and buffer exchange. The hTim-3-IgV-FLAG is purified from the 293HEK supernatant with a standard anti-FLAG resin (Sigma-Aldrich) protocol. The hTim-3-IgV domain represents amino acid residues S22 to K130 of human Tim-3 (SEQ ID:1). Flow through is rerun in the resin column multiple times. After each run, SDS-PAGE (NuPAGE Novex 4-12% Bis-Tris Gels; Invitrogen) and HPLC (TSK-gel G3000 SW XL (Dimensions: 7.8 mm, ID 30 CM, 5 μM; TOSHO BioSCIENCE) is utilized to determine quality of the hTim-3-FLAG protein. Proteins of the best rounds are combined together to generate the final batch.

hTim-3-IgV-FLAG, at 2.17 mg/mL in TBS buffer pH 7.2, and Antibody A-Fab, at 6.79 mg/mL, are combined in a 1:1 molar ratio and the complex is isolated via size exclusion chromatography with a final concentration of 6.9 mg/mL in 20 mM hepes pH 7.4 and 150 mM sodium chloride. The Tim-3-anti-Tim-3 complex is screened in five Qiagen grid screens at both 8° C. and 21° C. using the sitting drop vapor diffusion method. Drops are set up using an Art Robbins Phoenix liquid handling robot which dispenses 0.3 μL crystallization solution on top of 0.3 μL protein. 100-200 μm intergrown prisms are obtained at 21° C. in 20% PEG 3350 and 0.2 M lithium chloride. Crystals are harvested and cryoprotected in a solution made of the crystallization condition supplemented with 20% ethylene glycol prior to flash freezing in liquid nitrogen. A dataset is collected at Argonne National Laboratory diffracting to 2.2 Å in space group P21 with cell parameters a=74.62 Å, b=57.85 Å, and c=74.71 Å.

The structure of the Antibody A-Fab in complex with human Tim-3 is determined by Molecular Replacement using the program Phaser. High resolution and publicly available Fab structures and the published structure of murine Tim-3 can be used as Molecular Replacement models. The structure is refined using the program Refmac and the model rebuilt using the program COOT. Final refinement R-factors are Rwork=20.2%, Rfree=23.4%. There are no Ramachandran violators, and 96.4% of the residues are in the favored region of the Ramachandran plot. There is density indicating glycosylation at Asn99 of Tim-3 (SEQ ID NO:1).

Biacore T200 is utilized to determine the binding kinetics of hTim-3-IgV-FLAG to the captured AntibodyA-Fab. In

TABLE 3

| | Concentration of Antibody (nM) | | | | | | | | | |
|---|---|---|---|---|---|---|---|---|---|---|
| | 0.015 | 0.046 | 0.137 | 0.41 | 1.24 | 3.71 | 11.1 | 33.3 | 100 | 300 |
| Human IgG Control (O.D.) | 2.05 | 2.02 | 2.13 | 2.03 | 2.04 | 2.03 | 2.05 | 2.07 | 2.12 | 2.08 |
| Polyclonal Anti-Tim-3 (O.D.) | 1.96 | 1.88 | 1.89 | 1.88 | 1.85 | 1.80 | 1.51 | 1.16 | 0.99 | 0.99 |
| Antibody A (O.D.) | 1.87 | 1.88 | 1.87 | 1.82 | 1.80 | 1.78 | 1.79 | 1.79 | 1.73 | 1.74 |

HBS-EP as a running buffer, 1:1 binding of this complex at 25° C. has a $k_{on}$ of 3.62E+05 1/Ms, $k_{off}$ of 2.86E-03 1/s, and a $K_D$ of 7.92E-09 M.

In experiments performed essentially as described in this assay, Antibody A-Fab/hTim-3 complex is resolved and the epitope/paratope is illustrated in Table 4 below. Table 4 below lists the residues on Antibody A-Fab that are within 6 Å of the listed residues on hTim-3 (SEQ ID NO:1). The heavy chain of the Antibody A-Fab has 62 contacts (cutoff 6 Å) with hTim-3 while the light chain has 34 contacts (cutoff 6 Å).

TABLE 4

| Tim-3 (Epitope) | Antibody A Heavy Chain (Paratope) | Antibody A Light Chain (Paratope) |
|---|---|---|
| P50 | S54 | — |
| K55 | — | Y32 |
| G56 | — | Y32 |
| A57 | — | Y30, Y32, N92 |
| C58 | — | Y32, A91, N92, S93 |
| P59 | Y99, T102 | Y32, A91, N92, S93 |
| V60 | Y59, Y99, T102 | Y32, Q89, Q90, A91, N92, S93, F94, P95, P96 |
| F61 | Y33, S35, W47, A50, Y59, Y99, A100, T102, F104 | A91, F94, P96 |
| E62 | S31, Y33, Y59, Y99, R101 | — |
| C63 | Y99, R101, T102 | Y32 |
| G64 | T102 | Y32 |
| N65 | T102 | N31, Y32, A50 |
| E72 | S54 | — |
| I107 | — | T30 |
| R111 | Y33, Y59 | — |
| Q113 | Y33, S52, G53, S54, G55, G56, S57, Y59 | — |
| I114 | G56, S57 | — |
| P115 | G56, S57 | — |
| G116 | G56, S57, T58, Y59 | — |
| I117 | G56, S57, T58, Y59, Y60, K65 | — |
| M118 | S57, T58, Y59, Y60, A61, D62, K65 | F94 |
| N119 | T58, Y59 | — |
| D120 | Y33, S57, Y59 | — |
| K122 | — | N92, F94 |

Competition Assay

A competition assay can be performed to determine whether Antibody B and Antibody C compete with Antibody A for binding to human Tim-3. An Octet® Red384 instrument and AR2G (Amine Reactive Second Generation) Biosensors from ForteBIO can be used for this assay. Biosensors are rehydrated in $H_2O$ for a minimum of 30 minutes before being activated with 20 mM 1-Ethyl-3-(3-dimethylaminopropyl)-carbodiimide (EDC) and 10 mM N-hydroxysuccinimide (NHS) for 300 seconds. Antibodies at 2 ug/ml in 10 mM sodium acetate buffer, pH 4.5 are coupled to the sensor through free amines for 500 sec and the coupling reaction is quenched with 1M ethanolamine for 400 seconds. Sensors are dipped in kinase buffer (obtained from the AR2G reagent kit (ForteBIO)) for baseline measurement for 300 seconds. Sensors are then dipped into a 100 nM human Tim-3-IgV-Fc single arm antigen (SAG in kinase buffer for 500 sec to enable the binding of the antigen to amine coupled antibodies on the sensor. Next, sensors are dipped into 100 nM of test antibodies in kinase buffer for 300 seconds to test for competition. Sensograms are visualized using the ForteBio Data Analysis 8.0 software. Each trace is visually compared to its respective "self-self" control. If additional binding is observed when sensors are dipped into the test antibodies, the test antibody is considered not to compete with the antibody coupled to the sensor for binding to the antigen. If no additional binding is observed, the test antibody is considered to be blocked by or to compete with the fixed antibody for binding to the antigen.

In experiments performed essentially as described here, no additional binding is observed for either Antibody B or Antibody C when Antibody A is coupled to the sensor, and vice versa. These data demonstrate that Antibody B and Antibody C compete with Antibody A for binding to human Tim-3.

hTIM-3 DO11.10 Cell Based Assay Using Antibody A, Antibody B, and Antibody C

The ability for antibodies of the present invention to bind to cellular bound human Tim-3 and promote T cell activation can be measured using a human Tim-3 expressing DO11.10 cell line and measuring for IL-2 production. For the huma Tim-3 DO11.10 cell based assay, $2 \times 10^4$ cells/well (in 50 microliters) of either DO11.10 or DO11.10 cells expressing human Tim-3 are plated with $2 \times 10^4$ cells/well of A20 cells (in 50 microliters) in a 96 well U bottom tissue culture plate (Greiner CELLSTAR®) with RPMI 1640 media (Gibco®). 50 µl of OVA peptide (323-339) (Sigma-Aldrich®) is added to achieve a final concentration of 0.2 uM (diluted in media). Antibody A, Antibody B, Antibody C, or control human IgG is diluted into RPMI 1640 media starting from 200 nM with a dilution factor of 3 to give concentrations of 0.09, 0.27, 0.82, 2.47, 7.41, 22.2, 66.7 and 200 nM. 50 µl of the diluted Antibody A, Antibody B, Antibody C, or control human IgG is added to each well. RPMI 1640 media is then added as needed to achieve a final volume of 200 µl/well. Supernatants are collected 18-22 hours after stimulation and IL-2 levels in the supernatants are measured by ELISA (R&D Systems®). The EC50 is calculated with GraphPad software.

In experiments performed essentially as described above, Antibody A, Antibody B, and Antibody C enhance OVA-specific T cell activation in a dose-dependent manner with the EC50 values shown in Table 5.

TABLE 5

| | Antibody A | Antibody B | Antibody C |
|---|---|---|---|
| EC50 (nM) | 3.707 | 6.079 | 3.352 |

Kinetics/Affinity Study for Antibody A, Antibody B, and Antibody C

A Biacore T100 instrument can be used to measure the kinetics of human Tim-3-IgV-Fc single arm antigen (SAG) binding to captured Antibody A, Antibody B, or Antibody C. Human Fab Binder surfaces are prepared by amine-coupling Human Fab Binder (GE Healthcare) to a Biacore CM5 sensor chip surface. Test antibodies are captured by the chip using HBS-EP buffer (GE Healthcare) as the running buffer. Tim-3 SAG is diluted into running buffer starting at 30 nM with a dilution factor of 3 to give concentrations of 0.04, 0.12, 0.37, 1.11, 3.33, 10 and 30 nM. Diluted Tim-3 SAG analyte or buffer is injected at 30 µl/min for 180 seconds and the complex dissociation is monitored for 1200 seconds. The binding surface is regenerated with injection of 10 mM Glycine-HCl pH 2.1 at 30 µl/min, 30 seconds of two injections for five lower concentrations, and two injections at 60 seconds for two higher concentrations between each analyte binding cycle. Experimental data for a given antigen/Ab interaction are fit using a 1:1 Langmuir with mass transport Model.

In experiments performed essentially as described above, Antibody A, Antibody B, and Antibody C bind to human Tim-3 with the kinetics and affinity constants illustrated in Table 6.

TABLE 6

| Antibody | $K_{on}$ (1/Ms) | $K_{off}$ (1/s) | $K_D$ (M) | $R_{max}$ | Chi$^2$ |
|---|---|---|---|---|---|
| Antibody B | 6.75E+05 | 1.06E−04 | 1.58E−10 | 17.36 | 0.115 |
| Antibody C | 7.97E+05 | 1.38E−04 | 1.73E−10 | 32.56 | 0.404 |
| Antibody A | 2.33E+06 | 9.27E−04 | 3.98E−10 | 17.09 | 0.319 |

Antibody Generation, Expression, and Purification

The antibodies of the present invention may be generated by known methods including use of, but not limited to, phage display, transgenic animals, and humanization. Additionally, the antibodies derived as described above may be further screened using the assays described herein.

The polypeptides of the variable regions of the heavy chain and light chain, the complete heavy chain and light chain amino acid sequences of Antibodies A through C, and the nucleotide sequences encoding the same, are listed in the section entitled "Amino Acid and Nucleotide Sequences." In addition, the SEQ ID NOs for the light chain, heavy chain, light chain variable region, and heavy chain variable region of Antibodies A through C are shown in Table 7.

The antibodies of the present invention, including, but not limited to, Antibodies A through C can be made and purified essentially as follows. An appropriate host cell, such as HEK 293 or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by UV absorbance or SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is greater than 95%. The product may be immediately frozen at −70° C. or may be lyophilized.

TABLE 7

| Corresponding SEQ ID | Antibody A | Antibody B | Antibody C |
|---|---|---|---|
| HCDR1 | 2 | 14 | 26 |
| HCDR2 | 3 | 15 | 27 |
| HCDR3 | 4 | 16 | 28 |
| LCDR1 | 5 | 17 | 29 |
| LCDR2 | 6 | 18 | 30 |
| LCDR3 | 7 | 19 | 31 |
| HCVR | 8 | 20 | 32 |
| LCVR | 9 | 21 | 33 |
| Heavy chain | 10 | 22 | 34 |
| Light chain | 11 | 23 | 35 |
| DNA Heavy Chain | 12 | 24 | 36 |
| DNA Light Chain | 13 | 25 | 37 |

Amino Acid and Nucleotide Sequences (human Tim-3)
SEQ ID NO: 1
MFSHLPFDCVLLLLLLLLTRSSEVEYRAEVGQNAYLPCFYTPAAPGNLVP
VCWGKGACPVFECGNVVLRTDERDVNYWTSRYWLNGDFRKGDVSLTIENV
TLADSGIYCCRIQIPGIMNDEKFNLKLVIK (HCDR1 of Antibody A)
SEQ ID NO: 2
AASGFTFSSYYMS (HCDR2 of Antibody A)
SEQ ID NO: 3
AISGSGGSTYYADSVKG (HCDR3 of Antibody A)
SEQ ID NO: 4
ARYARTAFDL (LCDR1 of Antibody A)
SEQ ID NO: 5
QASQDIYNYLN (LCDR2 of Antibody A)
SEQ ID NO: 6
YAASSLQS (LCDR3 of Antibody A)
SEQ ID NO: 7
QQANSFPPT (HCVR of Antibody A)
SEQ ID NO: 8
EVQLLESGGGLVQPGGSLRLSCAASGFTFSSYYMSWVRQAPGKGLEWVSA
ISGSGGSTYYADSVKGRFTISRDNSKNTLYLQMNSLRAEDTAVYYCARYA
RTAFDLWGQGTLVTVSS (LCVR of Antibody A)
SEQ ID NO: 9
DIVMTQSPSSLSASVGDGVTITCQASQDIYNYLNWYQQKPGKAPKLLIYA
ASSLQSGVPSRFSGSGSGTDFTLTISSLQPEDFATYYCQQANSFPPTFGQ
GTKLEIK (HC of Antibody A)
SEQ ID NO: 10
EVQLLESGGGLVQPGGSLRLSCAASGFTFSSYYMSWVRQAPGKGLEWVSA

ISGSGGSTYYADSVKGRFTISRDNSKNTLYLQMNSLRAEDTAVYYCARYA

RTAFDLWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPEAEGAPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPSSIEKTISKAKGQPREPQVYT

LPPSREEMTKNQVSLTCLVKGFYPSDIAVEWESNGQPENNYKTTPPVLDS

-continued

DGSFFLYSKLTVDKSRWQQGNVFSCSVMHEALHNHYTQKSLSLSPGK (LC of Antibody A)
SEQ ID NO: 11
DIVMTQSPSSLSASVGDGVTITCQASQDIYNYLNWYQQKPGKAPKLLIYA
ASSLQSGVPSRFSGSGSGTDFTLTISSLQPEDFATYYCQQANSFPPTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC (DNA of HC of Antibody A)
SEQ ID NO: 12
GAGGTGCAGCTGTTGGAGTCTGGCGGAGGGCTGGTGCAGCCGGGAGGCAG
CCTCAGGCTGAGCTGCGCTGCGAGCGGGTTTACTTTCTCGTCGTACTATA
TGTCGTGGGTGAGACAAGCACCAGGTAAAGGACTTGAGTGGGTGTCCGCT
ATCTCAGGCAGCGGAGGATCCACCTACTACGCGGATTCAGTCAAGGGAAG
ATTCACTATCTCGCGCGACAATTCCAAGAACACCCTGTACCTCCAGATGA
ACTCGCTGCGGGCAGAAGATACGGCCGTGTACTACTGTGCCCGCTACGCC
CGGACCGCCTTCGACTTGTGGGGTCAGGGAACCCTGGTCACTGTCTCCTC
AGCTAGCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCACTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAGAGTTGAGCC
CAAATCTTGTGACAAAACTCACACATGCCCACCGTGCCCAGCACCTGAAG
CCGAGGGGGCACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTATGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAAGACTGGCTGAATGGCAA
GGAGTACAAGTGCAAGGTCTCCAACAAAGCCCTCCCATCCTCCATCGAGA
AAACCATCTCCAAAGCCAAAGGGCAGCCCCGAGAACCACAGGTGTACACC
CTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTATTCCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGCAAA (DNA of LC of Antibody A)
SEQ ID NO: 13
GACATCGTGATGACTCAAAGCCCTTCAAGCCTCTCGGCGTCAGTCGGTGA
TGGCGTGACCATTACCTGTCAAGCATCCCAAGACATCTACAACTACTTGA
ATTGGTACCAGCAGAAGCCAGGGAAAGCCCCGAAGCTGCTGATCTACGCC
GCCTCCTCACTTCAGAGCGGAGTGCCATCCCGCTTTTCCGGATCGGGGAG CGGAACGGATTTCACTCTGACCATCTCGTCGCTGCAACCGGAGGACTTCG
CGACTTACTATTGCCAGCAGGCTAACTCGTTCCCGCCCACTTTCGGACAG
GGCACCAAGCTCGAAATCAAACGAACTGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGT (HCDR1 of Antibody B)
SEQ ID NO: 14
AASGFSFSSFYFS (HCDR2 of Antibody B)
SEQ ID NO: 15
AISGNGRSTYYADSVKG (HCDR3 of Antibody B)
SEQ ID NO: 16
ARYYNTGFDL (LCDR1 of Antibody B)
SEQ ID NO: 17
QASEAIYGYLN (LCDR2 of Antibody B)
SEQ ID NO: 18
YAASSLPI (LCDR3 of Antibody B)
SEQ ID NO: 19
QQAYGFPPT (HCVR of Antibody B)
SEQ ID NO: 20
EVQLLESGGGLVQPGGSLRLSCAASGFSFSSFYFSWVRQAPGKGLEWVSA
ISGNGRSTYYADSVKGRFTISRDNSKNTLYLQMNSLRAEDTAVYYCARYY
NTGFDLWGQGTLVTVSS (LCVR of Antibody B)
SEQ ID NO: 21
DIVMTQSPSSLSASVGDGVTITCQASEAIYGYLNWYQQKPGKAPKLLIYA
ASSLPIGVPSRFSGSGSGTDFTLTISSLQPEDFATYYCQQAYGFPPTFGQ
GTKLEIK (HC of Antibody B)
SEQ ID NO: 22
EVQLLESGGGLVQPGGSLRLSCAASGFSFSSFYFSWVRQAPGKGLEWVSA
ISGNGRSTYYADSVKGRFTISRDNSKNTLYLQMNSLRAEDTAVYYCARYY
NTGFDLWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKRVEPKSCDKTHTCPPCPAPEAEGAPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPSSIEKTISKAKGQPREPQVYT
LPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK (LC of Antibody B)
SEQ ID NO: 23
DIVMTQSPSSLSASVGDGVTITCQASEAIYGYLNWYQQKPGKAPKLLIYA
ASSLPIGVPSRFSGSGSGTDFTLTISSLQPEDFATYYCQQAYGFPPTFGQ
GTKLEIKRTVAAPSVFIFPPSDEQLKSGTAVVCLLNNFYPREAKVQWKVD

NALQSGNSQESVTEQDSKDSTYSLSSTLTLSKADYEKHKVYACEVTHQGL

SPVTKSFNRGEC (DNA of HC of Antibody B)
SEQ ID NO: 24

GAGGTGCAGCTGCTGGAATCCGGAGGAGGACTGGTCCAGCCAGGAGGCAG

CCTGCGACTGTCCTGTGCCGCTTCTGGCTTCAGTTTTTCTAGTTTCTATT

TTTCCTGGGTGCGGCAGGCTCCCGGCAAGGGACTGGAGTGGGTCTCTGCA

ATCAGCGGCAACGGGCGTTCTACATACTATGCCGACAGTGTGAAAGGCAG

GTTTACCATTAGCCGGGACAACTCAAAGAATACACTGTACCTGCAGATGA

ACTCTCTGCGAGCCGAAGACACTGCCGTGTACTATTGCGCCCGGTATTAT

AATACCGGGTTCGATCTGTGGGGACAGGGCACCCTGGTGACAGTCTCATC

TGCTAGCACCAAGGGCCCATCGGTCTTCCCCCTGGCACCCTCCTCCAAGA

GCACCTCTGGGGGCACAGCGGCCCTGGGCTGCCTGGTCAAGGACTACTTC

CCCGAACCGGTGACGGTGTCGTGGAACTCAGGCGCACTGACCAGCGGCGT

GCACACCTTCCCGGCTGTCCTACAGTCCTCAGGACTCTACTCCCTCAGCA

GCGTGGTGACCGTGCCCTCCAGCAGCTTGGGCACCCAGACCTACATCTGC

AACGTGAATCACAAGCCCAGCAACACCAAGGTGGACAAGAGAGTTGAGCC

CAAATCTTGTGACAAAACTCACACATGCCCACCGTGCCCAGCACCTGAAG

CCGAGGGGGCACCGTCAGTCTTCCTCTTCCCCCCAAAACCCAAGGACACC

CTCATGATCTCCCGGACCCCTGAGGTCACATGCGTGGTGGTGGACGTGAG

CCACGAAGACCCTGAGGTCAAGTTCAACTGGTATGTGGACGGCGTGGAGG

TGCATAATGCCAAGACAAAGCCGCGGGAGGAGCAGTACAACAGCACGTAC

CGTGTGGTCAGCGTCCTCACCGTCCTGCACCAAGACTGGCTGAATGGCAA

GGAGTACAAGTGCAAGGTCTCCAACAAAGCCCTCCCATCCTCCATCGAGA

AAACCATCTCCAAAGCCAAAGGGCAGCCCCGAGAACCACAGGTGTACACC

CTGCCCCCATCCCGGGAGGAGATGACCAAGAACCAAGTCAGCCTGACCTG

CCTGGTCAAAGGCTTCTATCCCAGCGACATCGCCGTGGAGTGGGAGAGCA

ATGGGCAGCCGGAGAACAACTACAAGACCACGCCTCCCGTGCTGGACTCC

GACGGCTCCTTCTTCCTCTATTCCAAGCTCACCGTGGACAAGAGCAGGTG

GCAGCAGGGGAACGTCTTCTCATGCTCCGTGATGCATGAGGCTCTGCACA

ACCACTACACGCAGAAGAGCCTCTCCCTGTCTCCGGGCAAA (DNA of LC of Antibody B)
SEQ ID NO: 25

GACATCGTGATGACCCAGTCCCCAAGCTCCCTGAGCGCCAGCGTGGGAGA

CGGCGTCACCATCACATGCCAGGCCTCTGAAGCCATCTACGGCTATCTGA

ATTGGTACCAGCAGAAGCCAGGGAAAGCCCCCAAGCTGCTGATCTATGCC

GCTTCTAGTCTGCCGATCGGAGTGCCCAGTAGGTTCTCTGGGAGTGGATC

AGGCACAGACTTTACTCTGACCATTTCAAGCCTGCAGCCTGAGGATTTCG

CTACTTACTATTGCCAGCAGGCTTATGGGTTCCCCCCTACATTTGGGCAG

GGAACTAAACTGGAGATCAAGCGAACTGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGT (HCDR1 of Antibody C)
SEQ ID NO: 26

AASGFTFSSYYMS (HCDR2 of Antibody C)
SEQ ID NO: 27

AISGNGKSTYYADSVKG (HCDR3 of Antibody C)
SEQ ID NO: 28

ARYYNTGFDL (LCDR1 of Antibody C)
SEQ ID NO: 29

QASQDIYNYLN (LCDR2 of Antibody C)
SEQ ID NO: 30

YYASSIVS (LCDR3 of Antibody C)
SEQ ID NO: 31

QQANSFPPT (HCVR of Antibody C)
SEQ ID NO: 32

EVQLLESGGGLVQPGGSLRLSCAASGFTFSSYYMSWVRQAPGKGLEWVSA
ISGNGKSTYYADSVKGRFTISRDNSKNTLYLQMNSLRAEDTAVYYCARYY
NTGFDLWGQGTLVTVSS (LCVR of Antibody C)
SEQ ID NO: 33

DIVMTQSPSSLSASVGDGVTITCQASQDIYNYLNWYQQKPGKAPKLLIYY
ASSIVSGVPSRFSGSGSGTDFTLTISSLQPEDFATYYCQQANSFPPTFGQ
GTKLEIK (HC of Antibody C)
SEQ ID NO: 34

EVQLLESGGGLVQPGGSLRLSCAASGFTFSSYYMSWVRQAPGKGLEWVSA
ISGNGKSTYYADSVKGRFTISRDNSKNTLYLQMNSLRAEDTAVYYCARYY
NTGFDLWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKRVEPKSCDKTHTCPPCPAPEAEGAPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPSSIEKTISKAKGQPREPQVYT
LPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK (LC of Antibody C)
SEQ ID NO: 35

DIVMTQSPSSLSASVGDGVTITCQASQDIYNYLNWYQQKPGKAPKLLIYY
ASSIVSGVPSRFSGSGSGTDFTLTISSLQPEDFATYYCQQANSFPPTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC (DNA of HC of Antibody C)
SEQ ID NO: 36

GAGGTGCAGCTGCTGGAATCCGGAGGAGGACTGGTCCAGCCAGGAGGCAG

CCTGCGACTGTCCTGTGCCGCTTCTGGCTTCACTTTTTCTAGTTACTATA

-continued

TGTCCTGGGTGCGGCAGGCTCCCGGCAAGGGACTGGAGTGGGTCTCTGCA

ATCAGCGGCAACGGAAAATCTACATACTATGCCGACAGTGTGAAAGGCAG

GTTTACCATTAGCCGGGACAACTCAAAGAATACACTGTACCTGCAGATGA

ACTCTCTGCGAGCCGAAGACACTGCCGTGTACTATTGCGCCCGGTATTAT

AATACGGGGTTCGATCTGTGGGGACAGGGCACCCTGGTGACAGTCTCATC

TGCTAGCACCAAGGGCCCATCGGTCTTCCCCCTGGCACCCTCCTCCAAGA

GCACCTCTGGGGGCACAGCGGCCCTGGGCTGCCTGGTCAAGGACTACTTC

CCCGAACCGGTGACGGTGTCGTGGAACTCAGGCGCACTGACCAGCGGCGT

GCACACCTTCCCGGCTGTCCTACAGTCCTCAGGACTCTACTCCCTCAGCA

GCGTGGTGACCGTGCCCTCCAGCAGCTTGGGCACCCAGACCTACATCTGC

AACGTGAATCACAAGCCCAGCAACACCAAGGTGGACAAGAGAGTTGAGCC

CAAATCTTGTGACAAAACTCACACATGCCCACCGTGCCCAGCACCTGAAG

CCGAGGGGGCACCGTCAGTCTTCCTCTTCCCCCCAAAACCCAAGGACACC

CTCATGATCTCCCGGACCCCTGAGGTCACATGCGTGGTGGTGGACGTGAG

CCACGAAGACCCTGAGGTCAAGTTCAACTGGTATGTGGACGGCGTGGAGG

TGCATAATGCCAAGACAAAGCCGCGGGAGGAGCAGTACAACAGCACGTAC

CGTGTGGTCAGCGTCCTCACCGTCCTGCACCAAGACTGGCTGAATGGCAA

GGAGTACAAGTGCAAGGTCTCCAACAAAGCCCTCCCATCCTCCATCGAGA

AAACCATCTCCAAAGCCAAAGGGCAGCCCCGAGAACCACAGGTGTACACC

CTGCCCCCATCCCGGGAGGAGATGACCAAGAACCAAGTCAGCCTGACCTG

CCTGGTCAAAGGCTTCTATCCCAGCGACATCGCCGTGGAGTGGGAGAGCA

ATGGGCAGCCGGAGAACAACTACAAGACCACGCCTCCCGTGCTGGACTCC

GACGGCTCCTTCTTCCTCTATTCCAAGCTCACCGTGGACAAGAGCAGGTG

GCAGCAGGGGAACGTCTTCTCATGCTCCGTGATGCATGAGGCTCTGCACA

ACCACTACACGCAGAAGAGCCTCTCCCTGTCTCCGGGCAAA (DNA of LC of Antibody C)

SEQ ID NO: 37

GACATCGTGATGACCCAGTCCCCAAGCTCCCTGAGCGCCAGCGTGGGAGA

CGGCGTCACCATCACATGCCAGGCCTCTCAGGATATCTACAACTATCTGA

ATTGGTACCAGCAGAAGCCAGGGAAAGCCCCCAAGCTGCTGATCTATTAC

GCTTCTAGTATTGTCTCTGGAGTGCCCAGTAGGTTCTCTGGGAGTGGATC

AGGCACAGACTTTACTCTGACCATTTCAAGCCTGCAGCCTGAGGATTTCG

CTACTTACTATTGCCAGCAGGCAAACAGCTTCCCCCCTACATTTGGGCAG

GGAACTAAACTGGAGATCAAGCGAACTGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGT (Ovalbumin peptide 323-339)

SEQ ID NO: 38

ISQAVHAAHAEINEAGR (Human CEACAM1)

SEQ ID NO: 39

MGHLSAPLHRVRVPWQGLLLLTASLLTFWNPPTTAQLTTESMPFNVAEGKE

VLLLVHNLPQQLFGYSWYKGERVDGNRQIVGYAIGTQQATPGPANSGRET

IYPNASLLIQNVTQNDTGFYTLQVIKSDLVNEEATGQFHVYPELPKPSIS

SNNSNPVEDKDAVAFTCEPETQDTTYLWWINNQSLPVSPRLQLSNGNRTL

TLLSVTRNDTGPYECEIQNPVSANRSDPVTLNVTYGPDTPTISPSDTYYR

PGANLSLSCYAASNPPAQYSWLINGTFQQSTQELFIPNITVNNSGSYTCH

ANNSVTGCNRTTVKTIIVTELSPVVAKPQIKASKTTVTGDKDSVNLTCST

NDTGISIRWFFKNQSLPSSERMKLSQGNTTLSINPVKREDAGTYWCEVFN

PISKNQSDPIMLNVNYNALPQENGLSPGAIAGIVIGVVALVALIAVALAC

FLHFGKTGRASDQRDLTEHKPSVSNHTQDHSNDPPNKMNEVTYSTLNFEA

QQPTQPTSASPSLTATEIIYSEVKKQ (Human Galectin-9)

SEQ ID NO: 40

MAFSGSQAPYLSPAVPFSGTIQGGLQDGLQITVNGTVLSSSGTRFAVNFQ

TGFSGNDIAFHFNPRFEDGGYYVVCNTRQNGSWGPEERKTHMPFQKGMPFD

LCFLVQSSDFKVMVNGILFVQYFHRVPFHRVDTISVNGSVQLSYISFQPP

GVWPANPAPITQTVIHTVQSAPGQMFSTPAIPPMMYPHPAYPMPFITTIL

GGLYPSKSILLSGTVLPSAQRFHINLCSGNHIAFHLNPRFDENAVVRNTQ

IDNSWGSEERSLPRKMPFVRGQSFSVWILCEAHCLKVAVDGQHLFEYYHR

LRNLPTINRLEVGGDIQLTHVQT

---

We claim:

1. An antibody that binds human Tim-3 (SEQ ID NO:1), the antibody comprising HCDR1, HCDR2, HCDR3, LCDR1, LCDR2, and LCDR3 wherein:
   a) HCDR1 has the amino acid sequence of SEQ ID NO: 2, HCDR2 has the amino acid sequence of SEQ ID NO: 3, HCDR3 has the amino acid sequence of SEQ ID NO: 4, LCDR1 has the amino acid sequence of SEQ ID NO:5, LCDR2 has the amino acid sequence of SEQ ID NO:6, and LCDR3 has the amino acid sequence of SEQ ID NO:7;
   b) HCDR1 has the amino acid sequence of SEQ ID NO:14, HCDR2 has the amino acid sequence of SEQ ID NO:15, HCDR3 has the amino acid sequence of SEQ ID NO:16, LCDR1 has the amino acid sequence of SEQ ID NO:17, LCDR2 has the amino acid sequence of SEQ ID NO:18, and LCDR3 has the amino acid sequence of SEQ ID NO:19; or
   c) HCDR1 has the amino acid sequence of SEQ ID NO:26, HCDR2 has the amino acid sequence of SEQ ID NO:27, HCDR3 has the amino acid sequence of SEQ ID NO:28, LCDR1 has the amino acid sequence of SEQ ID NO:29, LCDR2 has the amino acid sequence of SEQ ID NO:30, and LCDR3 has the amino acid sequence of SEQ ID NO:31.

2. The antibody of claim 1, wherein HCDR1 has the amino acid sequence of SEQ ID NO: 2, HCDR2 has the amino acid sequence of SEQ ID NO: 3, HCDR3 has the amino acid sequence of SEQ ID NO: 4, LCDR1 has the amino acid sequence of SEQ ID NO:5, LCDR2 has the amino acid sequence of SEQ ID NO:6, and LCDR3 has the amino acid sequence of SEQ ID NO:7.

3. The antibody of claim 1, wherein HCDR1 has the amino acid sequence of SEQ ID NO:14, HCDR2 has the amino acid sequence of SEQ ID NO:15, HCDR3 has the amino acid sequence of SEQ ID NO:16, LCDR1 has the amino acid sequence of SEQ ID NO:17, LCDR2 has the amino acid sequence of SEQ ID NO:18, and LCDR3 has the amino acid sequence of SEQ ID NO:19.

4. The antibody of claim 1, wherein HCDR1 has the amino acid sequence of SEQ ID NO:26, HCDR2 has the amino acid sequence of SEQ ID NO:27, HCDR3 has the amino acid sequence of SEQ ID NO:28, LCDR1 has the amino acid sequence of SEQ ID NO:29, LCDR2 has the amino acid sequence of SEQ ID NO:30, and LCDR3 has the amino acid sequence of SEQ ID NO:31.

5. An antibody that binds human Tim-3, comprising a heavy chain variable region (HCVR) and a light chain variable region (LCVR), wherein:
   a) the HCVR has the amino acid sequence of SEQ ID NO: 8, and the LCVR has the amino acid sequence of SEQ ID NO: 9;
   b) the HCVR has the amino acid sequence of SEQ ID NO: 20, and the LCVR has the amino acid sequence of SEQ ID NO: 21; or
   c) the HCVR has the amino acid sequence of SEQ ID NO: 32, and the LCVR has the amino acid sequence of SEQ ID NO: 33.

6. The antibody of claim 5, wherein the HCVR has the amino acid sequence of SEQ ID NO: 8, and the LCVR has the amino acid sequence of SEQ ID NO: 9.

7. The antibody of claim 5, wherein the HCVR has the amino acid sequence of SEQ ID NO: 20, and the LCVR has the amino acid sequence of SEQ ID NO: 21.

8. The antibody of claim 5, wherein the HCVR has the amino acid sequence of SEQ ID NO: 32, and the LCVR has the amino acid sequence of SEQ ID NO: 33.

9. An antibody that binds human Tim-3, comprising a heavy chain (HC) and a light chain (LC), wherein:
   a. the HC has the amino acid sequence of SEQ ID NO: 10 and the LC has the amino acid sequence of SEQ ID NO: 11;
   b. the HC has the amino acid sequence of SEQ ID NO: 22 and the LC has the amino acid sequence of SEQ ID NO: 23; or
   c. the HC has the amino acid sequence of SEQ ID NO: 34 and the LC has the amino acid sequence of SEQ ID NO: 35.

10. The antibody of claim 9, wherein the HC has the amino acid sequence of SEQ ID NO: 10 and the LC has the amino acid sequence of SEQ ID NO: 11.

11. The antibody of claim 9, wherein the HC has the amino acid sequence of SEQ ID NO: 22 and the LC has the amino acid sequence of SEQ ID NO: 23.

12. The antibody of claim 9, wherein the HC has the amino acid sequence of SEQ ID NO: 34 and the LC has the amino acid sequence of SEQ ID NO: 35.

13. The antibody of claim 9, wherein the antibody has two of the heavy chain and two of the light chain.

14. The antibody of claim 13, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

15. The antibody of claim 14, wherein the antibody is glycosylated.

16. An isolated mammalian cell capable of expressing an antibody comprising a heavy chain (HC) and a light chain (LC), wherein:
   a. the HC has the amino acid sequence of SEQ ID NO: 10 and the LC has the amino acid sequence of SEQ ID NO: 11;
   b. the HC has the amino acid sequence of SEQ ID NO: 22 and the LC has the amino acid sequence of SEQ ID NO: 23; or
   c. the HC has the amino acid sequence of SEQ ID NO: 34 and the LC has the amino acid sequence of SEQ ID NO: 35.

17. The isolated mammalian cell of claim 16, wherein the HC has the amino acid sequence of SEQ ID NO: 10 and the LC has the amino acid sequence of SEQ ID NO: 11.

18. The isolated mammalian cell of claim 16, wherein the HC has the amino acid sequence of SEQ ID NO: 22 and the LC has the amino acid sequence of SEQ ID NO: 23.

19. The isolated mammalian cell of claim 16, wherein the HC has the amino acid sequence of SEQ ID NO: 34 and the LC has the amino acid sequence of SEQ ID NO: 35.

20. A process for producing an antibody comprising cultivating an isolated mammalian cell capable of expressing the antibody and recovering the antibody; wherein the antibody comprises a heavy chain (HC) and a light chain (LC), wherein:
   a. the HC has the amino acid sequence of SEQ ID NO: 10 and the LC has the amino acid sequence of SEQ ID NO: 11;
   b. the HC has the amino acid sequence of SEQ ID NO: 22 and the LC has the amino acid sequence of SEQ ID NO: 23; or
   c. the HC has the amino acid sequence of SEQ ID NO: 34 and the LC has the amino acid sequence of SEQ ID NO: 35.

21. The process of claim 20, wherein the HC has the amino acid sequence of SEQ ID NO: 10 and the LC has the amino acid sequence of SEQ ID NO: 11.

22. The process of claim 20, wherein the HC has the amino acid sequence of SEQ ID NO: 22 and the LC has the amino acid sequence of SEQ ID NO: 23.

23. The process of claim 20, wherein the HC has the amino acid sequence of SEQ ID NO: 34 and the LC has the amino acid sequence of SEQ ID NO: 35.

24. An antibody produced by the process of claim 20.

25. A pharmaceutical composition, comprising the antibody of claim 9 and an acceptable carrier, diluent, or excipient.

26. A method of treating cancer, comprising administering to a patient in need, thereof an effective amount of the antibody of claim 9.

27. The method of claim 26, wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

28. The method of claim 27, wherein the lung cancer is non-small cell lung cancer.

29. The method of claim 26, wherein the antibody is administered in simultaneous, separate, or sequential combination with ionizing radiation.

30. The method of claim 26, wherein the antibody is administered in simultaneous, separate, or sequential combination with one or more chemotherapeutic agents.

* * * * *

UNITED STATES PATENT AND TRADEMARK OFFICE
CERTIFICATE OF CORRECTION

PATENT NO. : 10,253,096 B2
APPLICATION NO. : 15/679190
DATED : April 9, 2019
INVENTOR(S) : Yi Zhang et al.

Page 1 of 1

It is certified that error appears in the above-identified patent and that said Letters Patent is hereby corrected as shown below:

In the Claims

Column 92, Line 9, in Claim 26, please delete "need," and insert --need--, therefor.

Signed and Sealed this
Eighteenth Day of June, 2019

Andrei Iancu
*Director of the United States Patent and Trademark Office*

SEQUENCE LISTING

<160> NUMBER OF SEQ ID NOS: 40

<210> SEQ ID NO 1
<211> LENGTH: 130
<212> TYPE: PRT
<213> ORGANISM: Homo sapiens

<400> SEQUENCE: 1

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln

```
                 20                  25                  30
Asn Ala Tyr Leu Pro Cys Phe Tyr Thr Pro Ala Ala Pro Gly Asn Leu
             35                  40                  45

Val Pro Val Cys Trp Gly Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
            115                 120                 125

Ile Lys
    130

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Ala Ala Ser Gly Phe Thr Phe Ser Ser Tyr Tyr Met Ser
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

<400> SEQUENCE: 3

Ala Ile Ser Gly Ser Gly Gly Ser Thr Tyr Tyr Ala Asp Ser Val Lys
1               5                   10                  15

Gly

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Ala Arg Tyr Ala Arg Thr Ala Phe Asp Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Gln Ala Ser Gln Asp Ile Tyr Asn Tyr Leu Asn
1               5                   10

<210> SEQ ID NO 6
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Tyr Ala Ala Ser Ser Leu Gln Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gln Gln Ala Asn Ser Phe Pro Pro Thr
1               5

<210> SEQ ID NO 8
<211> LENGTH: 117
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Arg Thr Ala Phe Asp Leu Trp Gly Gln Gly Thr Leu
            100                 105                 110

Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Synthetic Construct

<400> SEQUENCE: 9

Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Pro
                 85                  90                  95

Thr Phe Gly Gln Gly Thr Lys Leu Glu Ile Lys
            100                 105

<210> SEQ ID NO 10
<211> LENGTH: 447
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Tyr Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ala Arg Thr Ala Phe Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 11
<211> LENGTH: 214
<212> TYPE: PRT
<213> ORGANISM: Artificial Sequence
<220> FEATURE:
<223> OTHER INFORMATION: Synthetic Construct

<400> SEQUENCE: 11

Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 12
```

<211> LENGTH: 1341
<212> TYPE: DNA
<213> ORGANISM: Artificial Sequence
<220> FEATURE:
<223> OTHER INFORMATION: Synthetic Construct

<400> SEQUENCE: 12

| | | | | | |
|---|---|---|---|---|---|
| gaggtgcagc | tgttggagtc | tggcggaggg | ctggtgcagc | cgggaggcag | cctcaggctg | 60 |
| agctgcgctg | cgagcgggtt | tactttctcg | tcgtactata | tgtcgtgggt | gagacaagca | 120 |
| ccaggtaaag | gacttgagtg | ggtgtccgct | atctcaggca | gcggaggatc | cacctactac | 180 |
| gcggattcag | tcaagggaag | attcactatc | tcgcgcgaca | attccaagaa | caccctgtac | 240 |
| ctccagatga | actcgctgcg | ggcagaagat | acggccgtgt | actactgtgc | ccgctacgcc | 300 |
| cggaccgcct | tcgacttgtg | gggtcaggga | accctggtca | ctgtctcctc | agctagcacc | 360 |
| aagggcccat | cggtcttccc | cctggcaccc | tcctccaaga | gcacctctgg | gggcacagcg | 420 |
| gccctgggct | gcctggtcaa | ggactacttc | cccgaaccgg | tgacggtgtc | gtggaactca | 480 |
| ggcgcactga | ccagcggcgt | gcacaccttc | ccggctgtcc | tacagtcctc | aggactctac | 540 |
| tccctcagca | gcgtggtgac | cgtgccctcc | agcagcttgg | gcacccagac | ctacatctgc | 600 |
| aacgtgaatc | acaagcccag | caacaccaag | gtggacaaga | gagttgagcc | caaatcttgt | 660 |
| gacaaaactc | acacatgccc | accgtgccca | gcacctgaag | ccgaggggc | accgtcagtc | 720 |
| ttcctcttcc | ccccaaaacc | caaggacacc | ctcatgatct | cccggacccc | tgaggtcaca | 780 |
| tgcgtggtgg | tggacgtgag | ccacgaagac | cctgaggtca | agttcaactg | gtatgtggac | 840 |
| ggcgtggagg | tgcataatgc | caagacaaag | ccgcgggagg | agcagtacaa | cagcacgtac | 900 |
| cgtgtggtca | gcgtcctcac | cgtcctgcac | caagactggc | tgaatggcaa | ggagtacaag | 960 |
| tgcaaggtct | ccaacaaagc | cctcccatcc | tccatcgaga | aaaccatctc | caaagccaaa | 1020 |
| gggcagcccc | gagaaccaca | ggtgtacacc | ctgcccccat | cccgggagga | gatgaccaag | 1080 |
| aaccaagtca | gcctgacctg | cctggtcaaa | ggcttctatc | ccagcgacat | cgccgtggag | 1140 |
| tgggagagca | atgggcagcc | ggagaacaac | tacaagacca | cgcctcccgt | gctggactcc | 1200 |
| gacggctcct | tcttcctcta | ttccaagctc | accgtggaca | agagcaggtg | gcagcagggg | 1260 |
| aacgtcttct | catgctccgt | gatgcatgag | gctctgcaca | accactacac | gcagaagagc | 1320 |
| ctctccctgt | ctccgggcaa | a | | | | 1341 |

<210> SEQ ID NO 13
<211> LENGTH: 642
<212> TYPE: DNA
<213> ORGANISM: Artificial Sequence
<220> FEATURE:
<223> OTHER INFORMATION: Synthetic Construct

<400> SEQUENCE: 13

| | | | | | |
|---|---|---|---|---|---|
| gacatcgtga | tgactcaaag | cccttcaagc | ctctcggcgt | cagtcggtga | tggcgtgacc | 60 |
| attacctgtc | aagcatccca | agacatctac | aactacttga | attggtacca | gcagaagcca | 120 |
| gggaaagccc | cgaagctgct | gatctacgcc | gcctcctcac | ttcagagcgg | agtgccatcc | 180 |
| cgcttttccg | gatcggggag | cggaacggat | ttcactctga | ccatctcgtc | gctgcaaccg | 240 |
| gaggacttcg | cgacttacta | ttgccagcag | gctaactcgt | tcccgcccac | tttcggacag | 300 |
| ggcaccaagc | tcgaaatcaa | acgaactgtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 14
<211> LENGTH: 13
<212> TYPE: PRT
<213> ORGANISM: Artificial Sequence
<220> FEATURE:
<223> OTHER INFORMATION: Synthetic Construct

<400> SEQUENCE: 14

```
Ala Ala Ser Gly Phe Ser Phe Ser Ser Phe Tyr Phe Ser
1               5                   10
```

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

```
Ala Ile Ser Gly Asn Gly Arg Ser Thr Tyr Tyr Ala Asp Ser Val Lys
1               5                   10                  15
Gly
```

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

```
Ala Arg Tyr Tyr Asn Thr Gly Phe Asp Leu
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct

<400> SEQUENCE: 17

```
Gln Ala Ser Glu Ala Ile Tyr Gly Tyr Leu Asn
1               5                   10
```

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

```
Tyr Ala Ala Ser Ser Leu Pro Ile
1               5
```

<210> SEQ ID NO 19
<211> LENGTH: 9
<212> TYPE: PRT
<213> ORGANISM: Artificial Sequence

```
<220> FEATURE:
<223> OTHER INFORMATION: Synthetic Construct

<400> SEQUENCE: 19

Gln Gln Ala Tyr Gly Phe Pro Pro Thr
1               5

<210> SEQ ID NO 20
<211> LENGTH: 117
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Phe
            20                  25                  30

Tyr Phe Ser Trp Val Arg Gln Ala Pro Gly Lys Gly Leu Glu Trp Val
            35                  40                  45

Ser Ala Ile Ser Gly Asn Gly Arg Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asn Thr Gly Phe Asp Leu Trp Gly Gln Gly Thr Leu
            100                 105                 110

Val Thr Val Ser Ser
        115

<210> SEQ ID NO 21
<211> LENGTH: 107
<212> TYPE: PRT
<213> ORGANISM: Artificial Sequence
<220> FEATURE:
<223> OTHER INFORMATION: Synthetic Construct

<400> SEQUENCE: 21

Asp Ile Val Met Thr Gln Ser Pro Ser Ser Leu Ser Ala Ser Val Gly
1               5                   10                  15

Asp Gly Val Thr Ile Thr Cys Gln Ala Ser Glu Ala Ile Tyr Gly Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Pro Ile Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Gly Phe Pro Pro
                85                  90                  95

Thr Phe Gly Gln Gly Thr Lys Leu Glu Ile Lys
            100                 105

<210> SEQ ID NO 22
<211> LENGTH: 447
<212> TYPE: PRT
<213> ORGANISM: Artificial Sequence
<220> FEATURE:
```

<223> OTHER INFORMATION: Synthetic Construct

<400> SEQUENCE: 22

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Phe
            20                  25                  30

Tyr Phe Ser Trp Val Arg Gln Ala Pro Gly Lys Gly Leu Glu Trp Val
        35                  40                  45

Ser Ala Ile Ser Gly Asn Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asn Thr Gly Phe Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445
```

<210> SEQ ID NO 23
<211> LENGTH: 214
<212> TYPE: PRT
<213> ORGANISM: Artificial Sequence
<220> FEATURE:
<223> OTHER INFORMATION: Synthetic Construct

<400> SEQUENCE: 23

```
Asp Ile Val Met Thr Gln Ser Pro Ser Ser Leu Ser Ala Ser Val Gly
1               5                   10                  15
Asp Gly Val Thr Ile Thr Cys Gln Ala Ser Glu Ala Ile Tyr Gly Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Pro Ile Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Tyr Gly Phe Pro Pro
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 24
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 24
gaggtgcagc tgctggaatc cggaggagga ctggtccagc caggaggcag cctgcgactg    60
tcctgtgccg cttctggctt cagttttttct agtttctatt tttcctgggt gcggcaggct   120
cccggcaagg gactggagtg gtctctctgca atcagcggca acgggcgttc tacatactat   180
gccgacagtg tgaaaggcag gtttaccatt agccgggaca actcaaagaa tacactgtac   240

```
ctgcagatga actctctgcg agccgaagac actgccgtgt actattgcgc ccggtattat    300
aataccgggt tcgatctgtg gggacagggc accctggtga cagtctcatc tgctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgcactga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaag ccgaggggggc accgtcagtc    720 ttcctcttcc ccccaaaacc caaggacacc ctcatgatct cccggacccc tgaggtcaca    780
tgcgtggtgg tggacgtgag ccacgaagac cctgaggtca agttcaactg gtatgtggac    840
ggcgtggagg tgcataatgc caagacaaag ccgcgggagg agcagtacaa cagcacgtac    900
cgtgtggtca gcgtcctcac cgtcctgcac caagactggc tgaatggcaa ggagtacaag    960
tgcaaggtct ccaacaaagc cctcccatcc tccatcgaga aaaccatctc caaagccaaa   1020
gggcagcccc gagaaccaca ggtgtacacc ctgcccccat cccgggagga tgaccaag     1080 aaccaagtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta ttccaagctc accgtggaca gagcaggtg gcagcagggg    1260 aacgtcttct catgctccgt gatgcatgag gctctgcaca accactacac gcagaagagc   1320 ctctcccctgt ctccgggcaa a                                             1341

<210> SEQ ID NO 25
<211> LENGTH: 642
<212> TYPE: DNA
<213> ORGANISM: Artificial Sequence
<220> FEATURE:
<223> OTHER INFORMATION: Synthetic Construct

<400> SEQUENCE: 25
gacatcgtga tgacccagtc cccaagctcc ctgagcgcca gcgtgggaga cggcgtcacc     60
atcacatgcc aggcctctga agccatctac ggctatctga attggtacca gcagaagcca    120
gggaaagccc ccaagctgct gatctatgcc gcttctagtc tgccgatcgg agtgcccagt    180
aggttctctg ggagtggatc aggcacagac tttactctga ccatttcaag cctgcagcct    240
gaggatttcg ctacttacta ttgccagcag gcttatgggt tccccctac atttgggcag    300 ggaactaaac tggagatcaa gcgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

<400> SEQUENCE: 26
```

```
Ala Ala Ser Gly Phe Thr Phe Ser Ser Tyr Tyr Met Ser
1               5                   10
```

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

```
Ala Ile Ser Gly Asn Gly Lys Ser Thr Tyr Tyr Ala Asp Ser Val Lys
1               5                   10                  15

Gly
```

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

```
Ala Arg Tyr Tyr Asn Thr Gly Phe Asp Leu
1               5                   10
```

<210> SEQ ID NO 29
<211> LENGTH: 11
<212> TYPE: PRT
<213> ORGANISM: Artificial Sequence
<220> FEATURE:
<223> OTHER INFORMATION: Synthetic Construct

<400> SEQUENCE: 29

```
Gln Ala Ser Gln Asp Ile Tyr Asn Tyr Leu Asn
1               5                   10
```

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

```
Tyr Tyr Ala Ser Ser Ile Val Ser
1               5
```

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

```
Gln Gln Ala Asn Ser Phe Pro Pro Thr
1               5
```

<210> SEQ ID NO 32
<211> LENGTH: 117
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Gly Asn Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asn Thr Gly Phe Asp Leu Trp Gly Gln Gly Thr Leu
            100                 105                 110

Val Thr Val Ser Ser
            115

<210> SEQ ID NO 33
<211> LENGTH: 107
<212> TYPE: PRT
<213> ORGANISM: Artificial Sequence
<220> FEATURE:
<223> OTHER INFORMATION: Synthetic Construct

<400> SEQUENCE: 33

Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Ile Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105

<210> SEQ ID NO 34
<211> LENGTH: 447
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Gly Asn Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Tyr Tyr Asn Thr Gly Phe Asp Leu Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 35
<211> LENGTH: 214
<212> TYPE: PRT
<213> ORGANISM: Artificial Sequence
<220> FEATURE:
<223> OTHER INFORMATION: Synthetic Construct

<400> SEQUENCE: 35

Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Ile Val Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 36
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 36
gaggtgcagc tgctggaatc cggaggagga ctggtccagc caggaggcag cctgcgactg      60
tcctgtgccg cttctggctt cacttttttct agttactata tgtcctgggt gcggcaggct    120
cccggcaagg gactggagtg ggtctctgca atcagcggca acggaaaatc tacatactat    180
gccgacagtg tgaaaggcag gtttaccatt agccgggaca ctcaaagaa tacactgtac    240
ctgcagatga actctctgcg agccgaagac actgccgtgt actattgcgc ccggtattat    300
aatacggggt tcgatctgtg gggacagggc accctggtga cagtctcatc tgctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgctctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaag ccgaggggggc accgtcagtc    720

| | |
|---|---|
| ttcctcttcc cccaaaacc caaggacacc ctcatgatct cccggacccc tgaggtcaca | 780 |
| tgcgtggtgg tggacgtgag ccacgaagac cctgaggtca agttcaactg gtatgtggac | 840 |
| ggcgtggagg tgcataatgc caagacaaag ccgcgggagg agcagtacaa cagcacgtac | 900 |
| cgtgtggtca gcgtcctcac cgtcctgcac caagactggc tgaatggcaa ggagtacaag | 960 |
| tgcaaggtct ccaacaaagc cctcccatcc tccatcgaga aaaccatctc caaagccaaa | 1020 |
| gggcagcccc gagaaccaca ggtgtacacc ctgcccccat cccgggagga gatgaccaag | 1080 |
| aaccaagtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta ttccaagctc accgtggaca agagcaggtg gcagcagggg | 1260 |
| aacgtcttct catgctccgt gatgcatgag gctctgcaca accactacac gcagaagagc | 1320 |
| ctctcccctgt ctccgggcaa a | 1341 |

<210> SEQ ID NO 37
<211> LENGTH: 642
<212> TYPE: DNA
<213> ORGANISM: Artificial Sequence
<220> FEATURE:
<223> OTHER INFORMATION: Synthetic Construct

<400> SEQUENCE: 37

| | |
|---|---|
| gacatcgtga tgacccagtc cccaagctcc ctgagcgcca gcgtgggaga cggcgtcacc | 60 |
| atcacatgcc aggcctctca ggatatctac aactatctga attggtacca gcagaagcca | 120 |
| gggaaagccc ccaagctgct gatctattac gcttctagta ttgtctctgg agtgcccagt | 180 |
| aggttctctg ggagtggatc aggcacagac tttactctga ccatttcaag cctgcagcct | 240 |
| gaggatttcg ctacttacta ttgccagcag gcaaacagct tcccccctac atttgggcag | 300 |
| ggaactaaac tggagatcaa gcgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 38
<211> LENGTH: 17
<212> TYPE: PRT
<213> ORGANISM: Gallus gallus

<400> SEQUENCE: 38

Ile Ser Gln Ala Val His Ala Ala His Ala Glu Ile Asn Glu Ala Gly
1               5                   10                  15

Arg

<210> SEQ ID NO 39
<211> LENGTH: 526
<212> TYPE: PRT
<213> ORGANISM: Homo sapiens

<400> SEQUENCE: 39

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr

```
            20                  25                  30
Thr Ala Gln Leu Thr Thr Glu Ser Met Pro Phe Asn Val Ala Glu Gly
        35                  40                  45
Lys Glu Val Leu Leu Leu Val His Asn Leu Pro Gln Gln Leu Phe Gly
    50                  55                  60
Tyr Ser Trp Tyr Lys Gly Glu Arg Val Asp Gly Asn Arg Gln Ile Val
65                  70                  75                  80
Gly Tyr Ala Ile Gly Thr Gln Gln Ala Thr Pro Gly Pro Ala Asn Ser
                85                  90                  95
Gly Arg Glu Thr Ile Tyr Pro Asn Ala Ser Leu Leu Ile Gln Asn Val
            100                 105                 110
Thr Gln Asn Asp Thr Gly Phe Tyr Thr Leu Gln Val Ile Lys Ser Asp
        115                 120                 125
Leu Val Asn Glu Glu Ala Thr Gly Gln Phe His Val Tyr Pro Glu Leu
    130                 135                 140
Pro Lys Pro Ser Ile Ser Ser Asn Asn Ser Asn Pro Val Glu Asp Lys
145                 150                 155                 160
Asp Ala Val Ala Phe Thr Cys Glu Pro Glu Thr Gln Asp Thr Thr Tyr
                165                 170                 175
Leu Trp Trp Ile Asn Asn Gln Ser Leu Pro Val Ser Pro Arg Leu Gln
            180                 185                 190
Leu Ser Asn Gly Asn Arg Thr Leu Thr Leu Leu Ser Val Thr Arg Asn
        195                 200                 205
Asp Thr Gly Pro Tyr Glu Cys Glu Ile Gln Asn Pro Val Ser Ala Asn
    210                 215                 220
Arg Ser Asp Pro Val Thr Leu Asn Val Thr Tyr Gly Pro Asp Thr Pro
225                 230                 235                 240
Thr Ile Ser Pro Ser Asp Thr Tyr Tyr Arg Pro Gly Ala Asn Leu Ser
                245                 250                 255
Leu Ser Cys Tyr Ala Ala Ser Asn Pro Pro Ala Gln Tyr Ser Trp Leu
            260                 265                 270
Ile Asn Gly Thr Phe Gln Gln Ser Thr Gln Glu Leu Phe Ile Pro Asn
        275                 280                 285
Ile Thr Val Asn Asn Ser Gly Ser Tyr Thr Cys His Ala Asn Asn Ser
    290                 295                 300
Val Thr Gly Cys Asn Arg Thr Thr Val Lys Thr Ile Ile Val Thr Glu
305                 310                 315                 320
Leu Ser Pro Val Val Ala Lys Pro Gln Ile Lys Ala Ser Lys Thr Thr
                325                 330                 335
Val Thr Gly Asp Lys Asp Ser Val Asn Leu Thr Cys Ser Thr Asn Asp
            340                 345                 350
Thr Gly Ile Ser Ile Arg Trp Phe Phe Lys Asn Gln Ser Leu Pro Ser
        355                 360                 365
Ser Glu Arg Met Lys Leu Ser Gln Gly Asn Thr Thr Leu Ser Ile Asn
    370                 375                 380
Pro Val Lys Arg Glu Asp Ala Gly Thr Tyr Trp Cys Glu Val Phe Asn
385                 390                 395                 400
Pro Ile Ser Lys Asn Gln Ser Asp Pro Ile Met Leu Asn Val Asn Tyr
                405                 410                 415
Asn Ala Leu Pro Gln Glu Asn Gly Leu Ser Pro Gly Ala Ile Ala Gly
            420                 425                 430
Ile Val Ile Gly Val Val Ala Leu Val Ala Leu Ile Ala Val Ala Leu
        435                 440                 445
```

Ala Cys Phe Leu His Phe Gly Lys Thr Gly Arg Ala Ser Asp Gln Arg
450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510

Leu Thr Ala Thr Glu Ile Ile Tyr Ser Glu Val Lys Lys Gln
        515                 520                 525

<210> SEQ ID NO 40
<211> LENGTH: 323
<212> TYPE: PRT
<213> ORGANISM: Homo sapiens

<400> SEQUENCE: 40

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Phe His Ile
    210                 215                 220

Asn Leu Cys Ser Gly Asn His Ile Ala Phe His Leu Asn Pro Arg Phe
225                 230                 235                 240

Asp Glu Asn Ala Val Val Arg Asn Thr Gln Ile Asp Asn Ser Trp Gly
                245                 250                 255

Ser Glu Glu Arg Ser Leu Pro Arg Lys Met Pro Phe Val Arg Gly Gln
            260                 265                 270

Ser Phe Ser Val Trp Ile Leu Cys Glu Ala His Cys Leu Lys Val Ala
        275                 280                 285

Val Asp Gly Gln His Leu Phe Glu Tyr Tyr His Arg Leu Arg Asn Leu

```
                   290                 295                 300
Pro Thr Ile Asn Arg Leu Glu Val Gly Gly Asp Ile Gln Leu Thr His
305                 310                 315                 320

Val Gln Thr
```